(12) United States Patent
Kawasaki et al.

(10) Patent No.: US 8,835,873 B2
(45) Date of Patent: Sep. 16, 2014

(54) CONTINUOUS STERILIZATION SYSTEM

(71) Applicant: Airex Co., Ltd., Nagoya (JP)

(72) Inventors: Koji Kawasaki, Nagoya (JP); Daisuke Kakuda, Nagoya (JP); Mitsuo Kamino, Nagoya (JP); Norihiko Tsuji, Nagoya (JP); Jun Masudome, Nagoya (JP)

(73) Assignee: Airex Co., Ltd., Nagoya-shi, Aichi (JP)

( * ) Notice: Subject to any disclaimer, the term of this patent is extended or adjusted under 35 U.S.C. 154(b) by 0 days.

(21) Appl. No.: 14/110,094

(22) PCT Filed: Oct. 24, 2012

(86) PCT No.: PCT/JP2012/077478
§ 371 (c)(1),
(2), (4) Date: Oct. 4, 2013

(87) PCT Pub. No.: WO2013/062006
PCT Pub. Date: May 2, 2013

(65) Prior Publication Data
US 2014/0027651 A1  Jan. 30, 2014

(30) Foreign Application Priority Data

Oct. 26, 2011 (JP) ................................. 2011-234630

(51) Int. Cl.
| | |
|---|---|
| A61L 2/00 | (2006.01) |
| A61L 2/08 | (2006.01) |
| B65G 47/30 | (2006.01) |
| B65B 55/08 | (2006.01) |
| B65B 55/04 | (2006.01) |
| B65G 47/84 | (2006.01) |

(52) U.S. Cl.
CPC ................ *A61L 2/087* (2013.01); *B65G 47/30* (2013.01); *B65G 47/846* (2013.01); *B65B 55/08* (2013.01); *B65G 47/84* (2013.01); *B65B 55/04* (2013.01); *A61L 2202/23* (2013.01); *A61L 2/08* (2013.01)
USPC ............ 250/455.11; 250/454.11; 250/453.11; 250/492.1; 250/492.3

(58) Field of Classification Search
USPC ............... 250/453.11, 454.11, 455.11, 492.1, 250/492.3
See application file for complete search history.

(56) References Cited

U.S. PATENT DOCUMENTS

2009/0134338 A1* 5/2009 Eguchi et al. ............. 250/396 R

FOREIGN PATENT DOCUMENTS

| JP | 10-218133 A | 8/1998 |
|---|---|---|
| JP | 2006-6726 A | 1/2006 |
| JP | 2008-56268 A | 3/2008 |
| JP | 2011-514292 A | 5/2011 |

OTHER PUBLICATIONS

International Search Report for PCT/JP2012/077478 (English translation), 2012.

* cited by examiner

*Primary Examiner* — Nicole Ippolito
*Assistant Examiner* — Hanway Chang
(74) *Attorney, Agent, or Firm* — Quarles & Brady LLP; Gavin J. Milczarek-Desai

(57) ABSTRACT

A continuous sterilization system is provided which reliably supports a sterilization target so that the sterilization target is not tipped over during a sterilization process and can stably ensure uniform irradiation periods on any portion of inner and outer surfaces and moreover, a portion sterilized by electron beam irradiation is not contaminated again. The continuous sterilization system is provided with a first conveying means, a first electron beam accelerator, a second conveying means, a second electron beam accelerator, and a third electron beam accelerator.

10 Claims, 16 Drawing Sheets

CONTINUOUS STERILIZATION SYSTEM

TECHNICAL FIELD

The present invention relates to a continuous sterilization system which continuously sterilizes an outer surface and an inner surface of a product container used in a Pharmaceutical aseptic product manufacturing plant or the like with electron beam irradiation and conveys the product container after sterilization to a workroom in an aseptic environment.

BACKGROUND ART

A prefilled syringe or a vial filled with a pharmaceutical product in advance has been manufactured for convenience at medical fields. A work of filling these syringes and vials with pharmaceutical products is conducted in a filling workroom in an aseptic environment (hereinafter referred to as an aseptic workroom).

A product container such as a syringe and a vial used in this work is small in size but the quantity to be processed is large and can be continuously conveyed into the aseptic workroom from outside the workroom. At that time, in order to ensure the aseptic state of the syringe or the vial, they are conveyed into the aseptic workroom inline through a continuous sterilization system.

Sterilization means used in these continuous sterilization systems includes dry and high-temperature hot air, hydrogen peroxide gas, EOG (ethylene oxide gas), electron beam irradiation, Gamma(γ)-ray irradiation and the like. Among them, as a method capable of processing at a low temperature and leaving no remaining residues in articles to be sterilized and which is safe and easy to be handled, a method using a low-energy electron beam has been widely employed.

Moreover, the product containers such as syringes and vials need to be sterilized not only on an outer surface but also an opening portion to a portion on an inner surface in which a drug is to be filled. However, when these small product containers are continuously conveyed in the continuous sterilization system, there is a problem that the electron beam is not emitted to a portion in contact with a conveying member such as a conveyer or a lift and this portion is not sterilized.

Thus, in the following Patent Literature 1, as an electron-beam irradiation continuous sterilization system for performing electron beam irradiation from a vertical direction while the product container is being conveyed by a mesh conveyer, employment of a slide guide is proposed.

According to this method, the product container having been conveyed by the mesh conveyer in its traveling direction slides and moves on the mesh conveyer in a diagonally lateral direction along the slide guide. As a result, a position where a bottom surface of the product container and a mesh of the mesh conveyer are in contact with each other changes, and the electron beam emitted from below through the mesh conveyer irradiates the entire bottom surface of the product container.

CITATION LIST

Patent Literature

Patent Literature 1: U.S. Pat. No. 3,840,473

SUMMARY OF INVENTION

Technical Problem

The electron-beam irradiation continuous sterilization system of the above described Patent Literature 1 has the following problem. First, since the product container is made to slide and move by the slide guide against the traveling direction of the mesh conveyer, it is concerned that the product container might be tipped over on the mesh conveyer depending on the shape of the product container.

Moreover, the position where the bottom surface of the product container and the mesh of the mesh conveyer are in contact with each other is not made stable and irradiation time of the electron beam to the entire bottom surface does not become uniform. Furthermore, the bottom surface of the product container irradiated with the electron beam moves to the mesh upper surface which has been in contact with the bottom surface of the product container and has not been irradiated with the electron beam, and this portion is contaminated again.

Thus, the present invention has an object to solve the above described problems and to provide a continuous sterilization system in which a sterilization target is not tipped over during a sterilization process, uniform irradiation time can be ensured stably on any portion on the inner and outer surfaces, and a portion having been sterilized with electron beam irradiation is not contaminated again.

Solution to Problem

In order to solve the above described problems, the inventors have found as the result of keen examination that the above described object can be achieved by employing a plurality of means for supporting the sterilization targets and first, sterilizing other portions while supporting a predetermined portion and subsequently, by supporting this sterilized portion and sterilizing the portion previously supported and have completed the present invention.

That is, according to description of claim 1, a continuous sterilization system (100, 200) according to the present invention is provided with:

first conveying means (20) for continuously conveying a cylindrical container (B) by supporting the same from a side surface;

a first electron beam accelerator (E1) for emitting an electron beam from the bottom surface portion side of the cylindrical container during conveyance by this first conveying means;

second conveying means (30) for continuously conveying the cylindrical container by supporting the same from the bottom surface portion side having been sterilized by electron beam irradiation by the first electron beam accelerator while rotating the same along a cylindrical shaft core of the cylindrical container;

a second electron beam accelerator (E2) for emitting the electron beam over the entire periphery from the side surface portion side of the cylindrical container during conveyance by this second conveying means; and a third electron beam accelerator (E3) for emitting the electron beam from the opening portion side to an inner surface portion of the cylindrical container during of the cylindrical container conveyance by the first conveying means or the second conveying means.

According to the above described configuration, the continuous sterilization system according to the present invention employs an electron beam accelerator as sterilization means for sterilizing the entire inner and outer surfaces of the cylindrical container. The electron beam accelerator employed here is preferably a low energy type (with an acceleration voltage of approximately 40 to 200 kV, for example). The low-energy type electron beam accelerator has an X-ray amount secondarily generated is extremely lower than a highenergy type (with an acceleration voltage of approximately 5000 kV, for example). As a result, a heavy and thick protective wall (concrete or lead) for shielding a large quantity of X-rays is not required, but the apparatus size is small and can be easily incorporated in an aseptic workroom inline, whereby maintenance is facilitated.

In this low-energy type electron beam accelerator, since sterilization processing can be executed at a low temperature, even if the cylindrical container is made of plastic, the container is not damaged. Moreover, residues do not remain in the sterilized cylindrical container, and the accelerator is sterilizing means which is safe and easy to be handled.

Moreover, the continuous sterilization system according to the present invention employs a plurality of electron beam irradiators and sterilizes each portion of the cylindrical container, respectively. First, when an electron beam is emitted from the bottom surface portion side of the cylindrical container, the cylindrical container is supported from the side surfaces. Subsequently, when the electron beam is emitted from the side surface portion side of the cylindrical container, the cylindrical container is supported from the bottom surface portion side sterilized by the previous electron beam irradiation. Moreover, by rotating this cylindrical container along its cylindrical shaft core, the electron beam can be uniformly emitted over the entire periphery of the side surface portion. Furthermore, when the electron beam is emitted from the opening portion to the inner surface portion of the cylindrical container, the cylindrical container is supported either on the side surface or the bottom surface portion side.

As described above, since the electron beam is emitted to the portion not supported while the portion for supporting the cylindrical container is changed, uniform irradiation time can be ensured stably on any portion on the inner and outer surfaces and moreover, the portion having been sterilized by the electron beam irradiation is not contaminated again. Moreover, the cylindrical container is conveyed in the continuous sterilization system while being supported on any one of the portions all the time. As described above, since the cylindrical container being conveyed is reliably supported, the cylindrical container is not tipped over during the sterilization process.

Thus, the present invention can provide a continuous sterilization system in which a sterilization target is reliably supported and the sterilization target is not tipped over during the sterilization process, uniform irradiation time can be ensured stably on any portion on the inner and outer surfaces, and also, the portion having been sterilized by electron beam irradiation is not contaminated again.

Moreover, according to claim 2, a continuous sterilization system (300) according to the present invention is provided with:

second conveying means (30) for continuously conveying a cylindrical container (B) by supporting the same from a bottom surface portion side while rotating the same along a cylindrical shaft core of the cylindrical container;

a second electron beam accelerator (E2) for emitting an electron beam from the side surface portion side of the cylindrical container over the entire periphery during conveyance by this second conveying means;

first conveying means (20) for continuously conveying the cylindrical container by supporting the same from the side surface having been sterilized by electron beam irradiation by the second electron beam accelerator;

a first electron beam accelerator (E1) for emitting the electron beam from the bottom surface portion side of the cylindrical container during conveyance by this first conveying means; and a third electron beam accelerator (E3) for emitting the electron beam from the opening portion side to an inner surface portion of the cylindrical container during conveyance by the second conveying means or the first conveying means.

According to the above described configuration, the continuous sterilization system according to the present invention employs an electron beam accelerator or preferably a low-energy type electron beam accelerator as sterilizing means for sterilizing the entire inner and outer surfaces of the cylindrical container similarly to claim 1. As a result, a heavy and thick protective wall (concrete or lead) for shielding a large quantity of X-rays is not required, but the apparatus size is small and can be easily incorporated in an aseptic workroom inline, whereby maintenance is facilitated.

In this low-energy type electron beam accelerator, since sterilization processing can be executed at a low temperature, even if the cylindrical container is made of plastic, the container is not damaged. Moreover, residues do not remain in the sterilized cylindrical container, and the accelerator is sterilizing means which is safe and easy to be handled.

Moreover, the continuous sterilization system according to the present invention employs a plurality of electron beam irradiators and sterilizes each portion of the cylindrical container, respectively. First, when an electron beam is emitted from the side surface portion side of the cylindrical container, the cylindrical container is supported from the bottom surface portion side. Moreover, by rotating this cylindrical container along its cylindrical shaft core, the electron beam can be uniformly emitted over the entire periphery of the side surface portion. Subsequently, when the electron beam is emitted from the bottom surface portion side of the cylindrical container, the cylindrical container is supported from the side surface having been sterilized by the previous electron beam irradiation. Moreover, when the electron beam is emitted from the opening portion to the inner surface portion of the cylindrical container, the cylindrical container is supported either on the side surface or the bottom surface portion side.

As described above, since the electron beam is emitted to the portion not supported while the portion for supporting the cylindrical container is changed, uniform irradiation time can be ensured stably on any portion on the inner and outer surfaces and moreover, the portion having been sterilized by the electron beam irradiation is not contaminated again. Moreover, the cylindrical container is conveyed in the continuous sterilization system while being supported on any one of the portions all the time. As described above, since the cylindrical container being conveyed is reliably supported, the cylindrical container is not tipped over during the sterilization process.

Thus, the present invention can provide a continuous sterilization system in which a sterilization target is reliably supported and the sterilization target is not tipped over during the sterilization process, uniform irradiation time can be ensured stably on any portion on the inner and outer surfaces, and also, the portion having been sterilized by electron beam irradiation is not contaminated again.

Moreover, the present invention is, according to description of claim 3, a continuous sterilization system according to claim 1 or 2, characterized in that the first conveying means (20) has a star wheel (21) on which a plurality of support portions (21a), each supporting the cylindrical container from its side surface, are provided on an outer periphery; and a first rotating member (22) for rotating this star wheel around its center axis.

According to the above described configuration, the first conveying means has the star wheel and the first rotating member for rotating this. On the star wheel, the plurality of support portions, each supporting the cylindrical container from its side surface, are provided on the outer periphery. Since the cylindrical container can be reliably supported by this support portion, the sterilization target is not tipped over during the sterilization process.

Moreover, the first rotating member rotates the star wheel around its center axis. Since the support portions of the star wheel are provided at equal intervals and the star wheel is rotated at a constant speed by the first rotating member, a conveying speed of the cylindrical container supported from the side surface becomes constant, and the electron beam irradiation by the first electron beam accelerator from the bottom surface portion side and the electron beam irradiation by the third electron beam accelerator performed depending on the case from the opening portion side to the inner surface portion can stably ensure uniform irradiation periods.

Thus, in the invention described in claim 3, the working effects similar to the invention described in claim 1 or 2 can be achieved further specifically.

Moreover, the present invention is, according to description of claim 4, a continuous sterilization system according to any one of claims 1 to 3, characterized by including:

the second conveying means (30) has a suction member (31) for supporting the cylindrical container by vacuum-suctioning the same from the bottom surface;

a second rotating member (32) for rotating this suction member together with the cylindrical container supported by the suction member along the cylindrical shaft core of the cylindrical container; and a first transfer member (33) for transferring the suction member together with the cylindrical container supported by the suction member in a direction intersecting the cylindrical shaft core of the cylindrical container.

According to the above described configuration, the second conveying means has the suction member, the second rotating member for rotating the suction member, and the first transfer member for transferring the suction member. The suction member supports the cylindrical container by vacuum-suctioning the cylindrical container from its bottom surface. Since the cylindrical container can be reliably supported by this suction member, the sterilization target is not tipped over during the sterilization process.

Moreover, the second rotating member rotates the suction member together with the cylindrical container along its cylindrical shaft core. As described above, since the cylindrical container supported by the suction member is rotated along its cylindrical shaft core, the electron beam irradiation by the second electron beam accelerator from the side surface portion side is emitted uniformly over the entire periphery of the cylindrical container.

Furthermore, the first transfer member transfers the suction member together with the cylindrical container at a constant speed. Since the suction member is transferred by the first transfer member at a constant speed, the conveying speed of the cylindrical container supported by the suction member becomes constant, and the electron beam irradiation by the second electron beam accelerator from the side surface portion side and the electron beam irradiation by the third electron beam accelerator performed depending on the case from the opening portion side to the inner surface portion can stably ensure uniform irradiation periods.

Thus, in the invention described in claim 4, the working effects similar to the invention described in anyone of claims 1 to 3 can be achieved further specifically.

Moreover, the present invention is, according to description of claim 5, a continuous sterilization system according to any one of claims 1 to 3, characterized in that the second conveying means (130) has a chucking member (131) for supporting the cylindrical container from the bottom surface portion side by chucking;

a third rotating member (132) for rotating this chucking member together with the cylindrical container supported by the chucking member along the cylindrical shaft core of the cylindrical container; and a second transfer member (133) for transferring the chucking member together with the cylindrical container supported by the chucking member in a direction intersecting the cylindrical shaft core of the cylindrical container.

According to the above described configuration, the second conveying means has the chucking member, the third rotating member for rotating the chucking member, and the second transfer member for transferring the chucking member. The chucking member supports the cylindrical container by chucking the cylindrical container from its bottom surface portion side. Since the cylindrical container can be reliably supported by this chucking member, the sterilization target is not tipped over during the sterilization process.

Moreover, the third rotating member rotates the chucking member together with the cylindrical container along its cylindrical shaft core. As described above, since the cylindrical container supported by the chucking member is rotated along its cylindrical shaft core, the electron beam irradiation by the second electron beam accelerator from the side surface portion side is emitted uniformly over the entire periphery of the cylindrical container.

Furthermore, the second transfer member transfers the chucking member together with the cylindrical container at a constant speed. Since the chucking member is transferred by the second transfer member at a constant speed, the conveying speed of the cylindrical container supported by the chucking member becomes constant, and the electron beam irradiation by the second electron beam accelerator from the side surface portion side and the electron beam irradiation by the third electron beam accelerator performed depending on the case from the opening portion side to the inner surface portion can stably ensure uniform irradiation periods.

Thus, in the invention described in claim 5, the working effects similar to the invention described in anyone of claims 1 to 3 can be achieved further specifically.

Moreover, according to description of claim 6, a continuous sterilization system (100) according to the present invention is provided with:

a chamber (10) having a carrying-in port (11) for carrying in the cylindrical container (B) and a carrying-out port (12) for carrying out the same;

supply means (40) for supplying a plurality of the cylindrical containers carried into the chamber through the carrying-in port;

first conveying means (20) having a star wheel (21) on which a plurality of support portions (21a), each supporting the cylindrical container supplied by this supply means from its side surface, are provided on an outer periphery and a first rotating member (22) for rotating this star wheel around its center axis and continuously conveying the cylindrical container;

a first electron beam accelerator (E1) for emitting an electron beam from the bottom surface portion side of the cylindrical container during conveyance by this first conveying means;

first reversing means (50) for receiving the cylindrical container from the first conveying means and reversing its cylindrical shaft core by approximately 90 degrees;

second conveying means (30) having a suction member (31) for receiving the cylindrical container from this first reversing means and supporting the cylindrical container from a bottom surface by vacuum-suctioning, a second rotating member (32) for rotating this suction member together with the cylindrical container supported by the suction member along the cylindrical shaft core of the cylindrical container, and a first transfer member (33) for transferring the suction member together with the cylindrical container supported by the suction member in a direction intersecting the cylindrical shaft core of the cylindrical container and continuously conveying the cylindrical container;

a second electron beam accelerator (E2) for emitting the electron beam over the entire periphery from the side surface portion side of the cylindrical container during conveyance by this second conveying means;

a third electron beam accelerator (E3) for emitting the electron beam from the opening portion side to the inner surface portion of the cylindrical container during conveyance by the second conveying means;

second reversing means (60) for receiving the cylindrical container from the second conveying means and reversing its cylindrical shaft core by approximately 90 degrees again; and carrying-out means (70) for receiving the cylindrical container from this second reversing means and carrying out the cylindrical container to the outside of the chamber through the carrying-out port.

According to the above described configuration, the continuous sterilization system according to the present invention is provided with the supply means, the first conveying means, the first electron beam accelerator, the first reversing means, the second conveying means, the second electron beam accelerator, the third electron beam accelerator, the second reversing means, and the carrying-out means in the chamber having the carrying-in port and the carrying-out port of the cylindrical container in the chamber having the carrying-in port and the carrying-out port of the cylindrical container.

The cylindrical container introduced into the chamber through the carrying-in port of the chamber is delivered from the supply means to the first conveying means and sterilized from its bottom surface portion side by the electron beam irradiation by the first electron beam accelerator during conveyance by this first conveying means.

Subsequently, the cylindrical container whose bottom surface portion side has been sterilized by the electron beam irradiation by the first electron beam accelerator is delivered from the first conveying means to the first reversing means, has its cylindrical shaft core reversed by this first reversing means by approximately 90 degrees and is delivered to the second conveying means. At this time, in order that the bottom surface portion side which has been already sterilized is not contaminated by each member of the first reversing means and the second conveying means, the members in contact with the applicable portions are all in the sterilized state.

Subsequently, the cylindrical container is sterilized by the electron beam irradiation by the second electron beam accelerator over the entire periphery from the side surface portion side thereof during conveyance by the second conveying means. Moreover, the cylindrical container is sterilized by electron beam irradiation by the third electron beam accelerator on the inner surface portion from its opening portion side during conveyance by the second conveying means.

Subsequently, the cylindrical container whose entire inner and outer surfaces are sterilized is delivered from the second conveying means to the second reversing means, has its cylindrical shaft core reversed by this second reversing means by approximately 90 degrees again and is delivered to the carrying-out means. At this time, in order that the entire inner and outer surfaces having been already sterilized is not contaminated by each member of the second reversing means and the carrying-out means, the members in contact with the applicable portions are all in the sterilized state.

Subsequently, the cylindrical container is carried out by the carrying-out means to the outside of the chamber through the carrying-out port of the chamber. During such series of operations, the cylindrical container enters a state in which its entire inner and outer surfaces are reliably sterilized.

Moreover, the configurations and operations of the first conveying means and the second conveying means are similar to the contents explained in claims 3 and 4, and since the support portion of the star wheel provided in the first conveying means and the suction member provided in the second conveying means can reliably support the cylindrical container, the sterilization target is not tipped over during the sterilization process.

On the other hand, since the support portions of the star wheel provided in the first conveying means are provided at equal intervals, and since the star wheel is rotated by the first rotating member at a constant speed, the conveying speed of the cylindrical container supported from the side surface becomes constant, the electron beam irradiation by the first electron beam accelerator to the bottom surface portion can stably ensure a uniform irradiation period.

Moreover, since the second rotating member provided in the second conveying means rotates the suction member together with the cylindrical container along its cylindrical shaft core, the electron beam irradiation by the second electron beam accelerator from the side surface portion side is emitted uniformly over the entire periphery of the cylindrical container.

Furthermore, since the transfer member provided in the second conveying means transfers the suction member together with the cylindrical container at a constant speed, the conveying speed of the cylindrical container supported by the suction member is made constant, and the electron beam irradiation by the second electron beam accelerator to the side surface portion and the electron beam irradiation by the third electron beam accelerator from the opening portion side to the inner surface portion can stably ensure a uniform irradiation period.

Thus, in the invention described in claim 6, the working effects similar to those in the invention described in claim 1 can be achieved further specifically.

Moreover, according to description of claim 7, a continuous sterilization system (200) according to the present invention is provided with:

a chamber (10) having a carrying-in port (11) for carrying in the cylindrical container (B) and a carrying-out port (12) for carrying out the same;

supply means (40) for supplying a plurality of the cylindrical containers carried into the chamber through the carrying-in port;

first conveying means (20) having a star wheel (21) on which a plurality of support portions (21*a*), each supporting the cylindrical container supplied by this supply means from its side surface, are provided on an outer periphery and a first rotating member (22) for rotating this star wheel around its center axis and continuously conveying the cylindrical container;

a first electron beam accelerator (E1) for emitting an electron beam from the bottom surface portion side of the cylindrical container during conveyance by this first conveying means;

first reversing means (50) for receiving the cylindrical container from the first conveying means and reversing its cylindrical shaft core by approximately 90 degrees;

second conveying means (130) having a chucking member (131) for receiving the cylindrical container from this first reversing means and supporting the cylindrical container from the bottom surface portion side by chucking, a third rotating member (132) for rotating this chucking member together with the cylindrical container supported by the chucking member along the cylindrical shaft core of the cylindrical container, and a second transfer member (133) for transferring the chucking member together with the cylindrical container supported by the chucking member in a direction intersecting the cylindrical shaft core of the cylindrical container and continuously conveying the cylindrical container;

a second electron beam accelerator (E2) for emitting the electron beam over the entire periphery from the side surface portion side of the cylindrical container during conveyance by this second conveying means;

a third electron beam accelerator (E3) for emitting the electron beam from the opening portion to the inner surface portion side of the cylindrical container during conveyance by the second conveying means;

second reversing means (60) for receiving the cylindrical container from the second conveying means and reversing its cylindrical shaft core by approximately 90 degrees again; and carrying-out means (70) for receiving the cylindrical container from this second reversing means and carrying out the cylindrical container to the outside of the chamber through the carrying-out port.

According to the above described configuration, the continuous sterilization system according to the present invention is provided with the supply means, the first conveying means, the first electron beam accelerator, the first reversing means, the second conveying means, the second electron beam accelerator, the third electron beam accelerator, the second reversing means, and the carrying-out means in the chamber having the carrying-in port and the carrying-out port of the cylindrical container.

The cylindrical container introduced into the chamber through the carrying-in port of the chamber is delivered from the supply means to the first conveying means and sterilized from its bottom surface portion side by the electron beam irradiation by the first electron beam accelerator during conveyance by this first conveying means.

Subsequently, the cylindrical container whose bottom surface portion side has been sterilized by the electron beam irradiation by the first electron beam accelerator is delivered from the first conveying means to the first reversing means, has its cylindrical shaft core reversed by this first reversing means by approximately 90 degrees and is delivered to the second conveying means. At this time, in order that the bottom surface portion side which has been already sterilized is not contaminated by each member of the first reversing means and the second conveying means, the members in contact with the applicable portions are all in the sterilized state.

Subsequently, the cylindrical container is sterilized by the electron beam irradiation by the second electron beam accelerator over the entire periphery from the side surface portion side during conveyance by the second conveying means. Moreover, the cylindrical container is sterilized by electron beam irradiation by the third electron beam accelerator on the inner surface portion from its opening portion side during conveyance by the second conveying means.

Subsequently, the cylindrical container whose entire inner and outer surfaces are sterilized is delivered from the second conveying means to the second reversing means, has its cylindrical shaft core reversed by this second reversing means by approximately 90 degrees again and is delivered to the carrying-out means. At this time, in order that the entire inner and outer surfaces having been already sterilized is not contaminated by each member of the second reversing means and the carrying-out means, the members in contact with the applicable portions are all in the sterilized state.

Subsequently, the cylindrical container is carried out by the carrying-out means to the outside of the chamber through the carrying-out port of the chamber. During such series of operations, the cylindrical container enters a state in which its entire inner and outer surfaces are reliably sterilized.

Moreover, the configurations and operations of the first conveying means and the second conveying means are similar to the contents explained in claims 3 and 5, and since the support portion of the star wheel provided in the first conveying means and the chucking member provided in the second conveying means can reliably support the cylindrical container, the sterilization target is not tipped over during the sterilization process.

On the other hand, since the support portions of the star wheel provided in the first conveying means are provided at equal intervals, and since the star wheel is rotated by the first rotating member at a constant speed, the conveying speed of the cylindrical container supported from the side surface becomes constant, the electron beam irradiation by the first electron beam accelerator to the bottom surface portion can stably ensure a uniform irradiation period.

Moreover, since the third rotating member provided in the second conveying means rotates the chucking member together with the cylindrical container along its cylindrical shaft core, the electron beam irradiation by the second electron beam accelerator from the side surface portion side is emitted uniformly over the entire periphery of the cylindrical container.

Furthermore, since the transfer member provided in the second conveying means transfers the chucking member together with the cylindrical container at a constant speed, the conveying speed of the cylindrical container supported by the chucking member is made constant, and the electron beam irradiation by the second electron beam accelerator to the side surface portion and the electron beam irradiation by the third electron beam accelerator from the opening portion side to the inner surface portion can stably ensure a uniform irradiation period.

Thus, in the invention described in claim 7, the working effects similar to those in the invention described in claim 1 can be achieved further specifically.

Moreover, according to description of claim 8, a continuous sterilization system (300) according to the present invention is provided with:

a chamber (10) having a carrying-in port (11) for carrying in the cylindrical container (B) and a carrying-out port (12) for carrying out the same;

supply means (40) for supplying a plurality of the cylindrical containers carried into the chamber through the carrying-in port;

first reversing means (80) for receiving the cylindrical container from the supply means and reversing its cylindrical shaft core by approximately 90 degrees;

second conveying means (30) having a suction member (31) for receiving the cylindrical container from this first reversing means and supporting the cylindrical container from a bottom surface by vacuum-suctioning, a second rotating member (32) for rotating this suction member together with the cylindrical container supported by the suction member along the cylindrical shaft core of the cylindrical container, and a first transfer member (33) for transferring the suction member together with the cylindrical container supported by the suction member in a direction intersecting the cylindrical shaft core of the cylindrical container and continuously conveying the cylindrical container;

a second electron beam accelerator (E2) for emitting the electron beam over the entire periphery from the side surface portion side of the cylindrical container during conveyance by this second conveying means;

a third electron beam accelerator (E3) for emitting the electron beam from the opening portion side to the inner surface portion of the cylindrical container during conveyance by the second conveying means;

second reversing means (60) for receiving the cylindrical container from the second conveying means and reversing its cylindrical shaft core by approximately 90 degrees again;

first conveying means (20) having a star wheel (21) on which a plurality of support portions (21*a*), each supporting the cylindrical container from its side surface, are provided on an outer periphery, and a first rotating member (22) for rotating this star wheel around its center axis and continuously conveying the cylindrical container;

a first electron beam accelerator (E1) for emitting an electron beam from the bottom surface portion side of the cylindrical container during conveyance by this first conveying means; and carrying-out means (70) for receiving the cylindrical container from the first conveying means and carrying out the cylindrical container to the outside of the chamber through the carrying-out port.

According to the above described configuration, the continuous sterilization system according to the present invention is provided with the supply means, the first reversing means, the second conveying means, the second electron beam accelerator, the third electron beam accelerator, the second reversing means, the first conveying means, the first electron beam accelerator, and the carrying-out means in the chamber having the carrying-in port and the carrying-out port of the cylindrical container.

The cylindrical container introduced into the chamber through the carrying-in port of the chamber is delivered from the supply means to the first reversing means, has its cylindrical shaft core reversed by this first reversing means by approximately 90 degrees and is delivered to the second conveying means. The cylindrical container delivered to this second conveying means is sterilized over the entire periphery from its side surface portion side by the electron beam irradiation by the second electron beam accelerator during conveyance by the second conveying means. Moreover, the cylindrical container is sterilized by the electron beam irradiation by the third electron beam accelerator from its opening portion side to the inner surface portion during conveyance by the second conveying means.

Subsequently, the cylindrical container sterilized on the entire periphery of the side surface portion and the inner surface portion is delivered from the second conveying means to the second reversing means, has its cylindrical shaft core reversed again by approximately 90 degrees by this second reversing means and is delivered to the first conveying means. At this time, in order that the side surface portion entire periphery and the inner surface portion which have been already sterilized are not contaminated by each member of the second reversing means and the first reversing means, the members in contact with the applicable portions are all in the sterilized state.

The cylindrical container sterilized on the side surface portion entire periphery and the inner surface portion is sterilized by the electron beam irradiation by the first electron beam accelerator from its bottom surface portion side during conveyance by the first conveying means. Subsequently, the cylindrical container is delivered from the first conveying means to the carrying-out means and is carried out by this carrying-out means to the outside of the chamber through the carrying-out port of the chamber. During such series of operations, the cylindrical container enters a state in which its entire inner and outer surfaces are reliably sterilized.

Moreover, the configurations and operations of the first conveying means and the second conveying means are similar to the contents explained in claims 3 and 4, and since the support portion of the star wheel provided in the first conveying means and the suction member provided in the second conveying means can reliably support the cylindrical container, the sterilization target is not tipped over during the sterilization process.

On the other hand, since the second rotating member provided in the second conveying means rotates the suction member together with the cylindrical container along its cylindrical shaft core, the electron beam irradiation by the second electron beam accelerator from the side surface portion side is emitted uniformly over the entire periphery of the cylindrical container.

Moreover, since the transfer member provided in the second conveying means transfers the suction member together with the cylindrical container at a constant speed, the conveying speed of the cylindrical container supported by the suction member is made constant, and the electron beam irradiation by the second electron beam accelerator to the side surface portion and the electron beam irradiation by the third electron beam accelerator from the opening portion side to the inner surface portion can stably ensure a uniform irradiation period.

Furthermore, since the support portions of the star wheel provided in the first conveying means are provided at equal intervals, and since the star wheel is rotated by the first rotating member at a constant speed, the conveying speed of the cylindrical container supported from the side surface becomes constant, the electron beam irradiation by the first electron beam accelerator to the bottom surface portion can stably ensure a uniform irradiation period.

Thus, in the invention described in claim 8, the working effects similar to those in the invention described in claim 1 can be achieved further specifically.

Moreover, according to description of claim 9, a continuous sterilization system (300) according to the present invention is provided with:

a chamber (10) having a carrying-in port (11) for carrying in the cylindrical container (B) and a carrying-out port (12) for carrying out the same;

supply means (40) for supplying a plurality of the cylindrical containers carried into the chamber through the carrying-in port;

first reversing means (80) for receiving the cylindrical container from the supply means and reversing its cylindrical shaft core by approximately 90 degrees;

second conveying means (130) having a chucking member (131) for receiving the cylindrical container from this first reversing means and supporting the cylindrical container from the bottom surface portion side by chucking, a third rotating member (132) for rotating this chucking member together with the cylindrical container supported by the chucking member along the cylindrical shaft core of the cylindrical container, and a second transfer member (133) for transferring the chucking member together with the cylindrical container supported by the chucking member in a direction intersecting the cylindrical shaft core of the cylindrical container and continuously conveying the cylindrical container;

a second electron beam accelerator (E2) for emitting the electron beam over the entire periphery from the side surface portion side of the cylindrical container during conveyance by this second conveying means;

a third electron beam accelerator (E3) for emitting the electron beam from the opening portion side to the inner surface portion of the cylindrical container during conveyance by the second conveying means;

second reversing means (60) for receiving the cylindrical container from the second conveying means and reversing its cylindrical shaft core by approximately 90 degrees again;

first conveying means (20) having a star wheel (21) on which a plurality of support portions (21a), each receiving the cylindrical container and supporting the cylindrical container from its side surface are provided on an outer periphery, are provided and a first rotating member (22) for rotating this star wheel around its center axis and continuously conveying the cylindrical container;

a first electron beam accelerator (E1) for emitting an electron beam from the bottom surface portion side of the cylindrical container during conveyance by this first conveying means; and carrying-out means (70) for receiving the cylindrical container from the first conveying means and carrying out the cylindrical container to the outside of the chamber through the carrying-out port.

According to the above described configuration, the continuous sterilization system according to the present invention is provided with the supply means, the first reversing means, the second conveying means, the second electron beam accelerator, the third electron beam accelerator, the second reversing means, the first conveying means, the first electron beam accelerator, and the carrying-out means in the chamber having the carrying-in port and the carrying-out port of the cylindrical container.

The cylindrical container introduced into the chamber through the carrying-in port of the chamber is delivered from the supply means to the first reversing means, has its cylindrical shaft core reversed by this first reversing means by approximately 90 degrees and is delivered to the second conveying means. The cylindrical container delivered to this second conveying means is sterilized over the entire periphery from its side surface portion side by the electron beam irradiation by the second electron beam accelerator during conveyance by the second conveying means. Moreover, the cylindrical container is sterilized by the electron beam irradiation by the third electron beam accelerator from its opening portion side to the inner surface portion during conveyance by the second conveying means.

Subsequently, the cylindrical container sterilized on the entire periphery of the side surface portion and the inner surface portion is delivered from the second conveying means to the second reversing means, has its cylindrical shaft core reversed again by approximately 90 degrees by this second reversing means and is delivered to the first conveying means. At this time, in order that the side surface portion entire periphery and the inner surface portion which have been already sterilized are not contaminated by each member of the second reversing means and the first conveying means, the members in contact with the applicable portions are all in the sterilized state.

The cylindrical container sterilized on the side surface portion entire periphery and the inner surface portion is sterilized by the electron beam irradiation by the first electron beam accelerator from its bottom surface portion side during conveyance by the first conveying means. Subsequently, the cylindrical container is delivered from the first conveying means to the carrying-out means and is carried out by this carrying-out means to the outside of the chamber through the carrying-out port of the chamber. During such series of operations, the cylindrical container enters a state in which its entire inner and outer surfaces are reliably sterilized.

Moreover, the configurations and operations of the first conveying means and the second conveying means are similar to the contents explained in claims 3 and 5, and since the support portion of the star wheel provided in the first conveying means and the chucking member provided in the second conveying means can reliably support the cylindrical container, the sterilization target is not tipped over during the sterilization process.

On the other hand, since the third rotating member provided in the second conveying means rotates the chucking member together with the cylindrical container along its cylindrical shaft core, the electron beam irradiation by the second electron beam accelerator from the side surface portion side is emitted uniformly to the entire periphery of the cylindrical container.

Moreover, since the transfer member provided in the second conveying means transfers the chucking member together with the cylindrical container at a constant speed, the conveying speed of the cylindrical container supported by the chucking member becomes constant, the electron beam irradiation by the second electron beam accelerator to the side surface portion and the electron beam irradiation by the third electron beam accelerator from the opening portion side to the inner surface portion can stably ensure a uniform irradiation period.

Furthermore, since the support portions of the star wheel provided in the first conveying means are provided at equal intervals, and since the star wheel is rotated by the first rotating member at a constant speed, the conveying speed of the cylindrical container supported from the side surface becomes constant, the electron beam irradiation by the first electron beam accelerator to the bottom surface portion can stably ensure a uniform irradiation period.

Thus, in the invention described in claim 9, the working effects similar to those in the invention described in claim 1 can be achieved further specifically.

Here, the term "sterilization" in the present invention does not mean only "sterilization" in the original definition but is a concept widely including "decontamination", too.

The "sterilization" in the original definition is, according to "Guideline relating to the aseptic drug products produced by aseptic processing" (so-called Japanese guideline on aseptic processing), defined as "Method of obtaining a state in which no microorganisms are present at all in a substance as a target by terminating or removing all the types of microorganisms whether it is a pathogen or a nonpathogen".

However, since it is not possible to reduce the number of germs to zero in terms of probabilistic concept, a Sterility Assurance Level (SAL) is employed in practice. Therefore, the "sterilization" according to the original definition is defined as termination or removal of all the types of microorganisms from a sterilization target and as a guarantee of $SAL \leq 10^{-12}$ level in some cases. As a sterilization method which can guarantee this level, a method of setting a required dose in electron beam irradiation to 25 kGy, for example (See ISO-13409) and the like can be used.

On the other hand, the term "decontamination" according to the original definition is defined as "to remove or reduce living microorganisms or particulates to a level designated in advance by a reproducible method" in the Japanese guideline on aseptic processing.

Therefore, the "decontamination" according to the original definition is defined as reduction of the living microorganisms from the sterilization target and a guarantee of $SAL \leq 10^{-6}$ level in some cases. As a sterilization method which can guarantee this level, electron beam irradiation with the required dose reduced to not more than 25 kGy, for example, can be used.

Thus, in the present invention, since an operation at the "decontamination" level according to the original definition is also possible in addition to the level of "sterilization" according to the original definition by controlling an output of the electron beam accelerator, the "sterilization" in the present invention is assumed to be a concept widely including "decontamination" as described above.

Reference numerals in parentheses of each of the above described means indicate correspondence to specific means described in embodiments which will be described later.

DESCRIPTION OF EMBODIMENTS

First Embodiment

Figure 1:
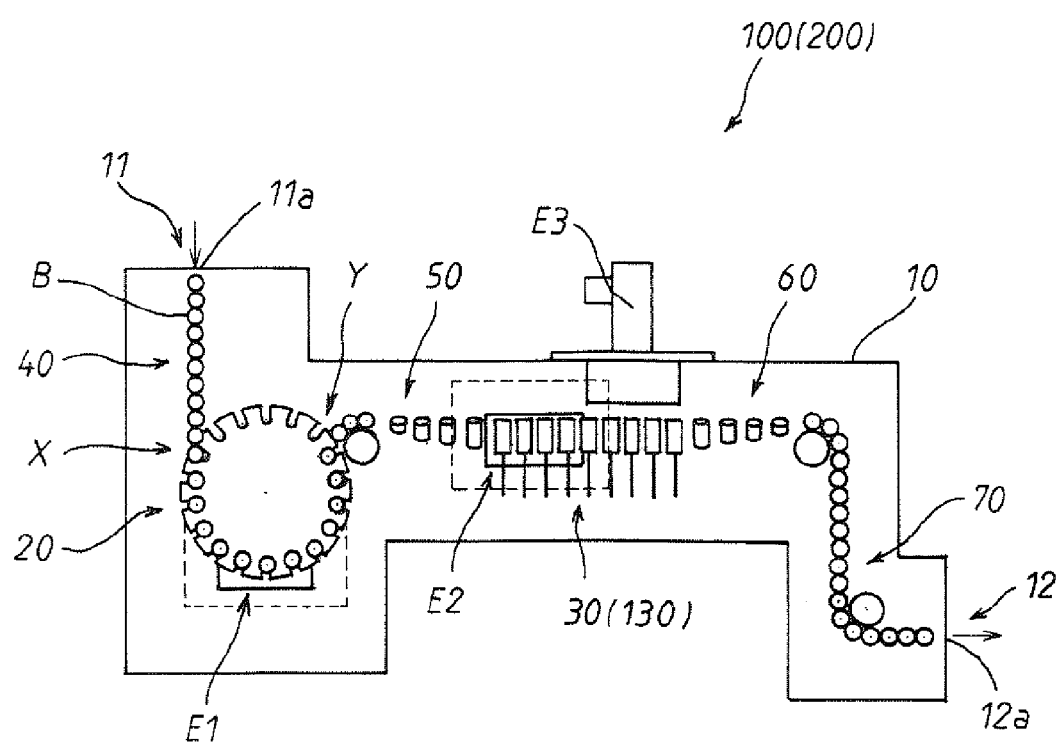
FIG. 1 is a plan view illustrating an outline of a continuous sterilization system according to a first embodiment.

A first embodiment of a continuous sterilization system according to the present invention will be described below in accordance with the attached drawings. FIG. 1 is a plan view of the continuous sterilization system 100 according to the first embodiment, and this continuous sterilization system 100 is formed of a chamber 10 constituted by a wall portion formed of a metal plate made of stainless in which an X-ray shielding material (not shown) is bonded inside and is installed consecutively to an aseptic workroom (not shown) in which a pharmaceutical product is filled on a right-side side surface in the illustration.

On a left-side rear surface of the chamber 10 (upper left side in FIG. 1), a carrying-in port 11 through which a cylindrical container B to be sterilized is carried into the chamber 10 is provided, and a shutter 11a capable for being opened/closed is provided at this carrying-in port 11. Moreover, on the right-side side surface of the chamber 10, a carrying-out port 12 through which the sterilized cylindrical container B is carried out of the chamber 10 into the aseptic workroom (not shown) installed consecutively is provided, and a shutter 12a capable of being opened/closed is provided at this carrying-out port 12.

In this first embodiment, in order to prevent entry of germs into the aseptic workroom in which a filling work is performed, an air pressure in the aseptic workroom is controlled to be higher than that of an outside environment. As a result, clean air in the aseptic workroom flows into the chamber 10 through the carrying-out port 12 and flows out to the outside environment through the carrying-in port 11. Thus, a flow of air from the right side to the left side in the figure is formed in the chamber 10, and the inside of the aseptic workroom is not contaminated.

Figure 2:
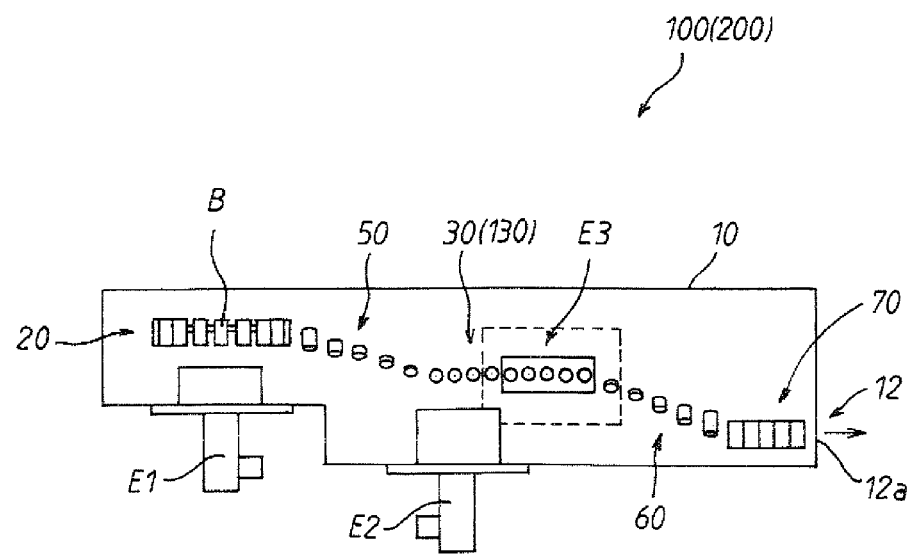
FIG. 2 is a front view illustrating an outline of the continuous sterilization system according to the first embodiment.

Inside the chamber 10, as illustrated in FIGS. 1 and 2, a star-wheel conveyer mechanism 20 and an adsorption conveyer mechanism 30 for supporting and conveying the cylindrical container B (See FIG. 3) for electron beam irradiation and three electron beam accelerators E1, E2, and E3 for sterilization by emitting electron beams to each portion of the cylindrical container B being conveyed by them are provided.

Moreover, inside the chamber 10, as illustrated in FIGS. 1 and 2, a belt conveyer mechanism 40 for conveying the cylindrical container B from the carrying-in port 11 to the star-wheel conveyer mechanism 20, a spiral chute mechanism 50 for delivery from the star-wheel conveyer mechanism 20 to the adsorption conveyer mechanism 30, a spiral chute mechanism 60 for receiving the cylindrical container B from the adsorption conveyer mechanism 30, and a belt conveyer mechanism 70 for receiving the cylindrical container B from this spiral chute mechanism 60 and conveying it to the carrying-out port 12 are provided.

Figure 3:
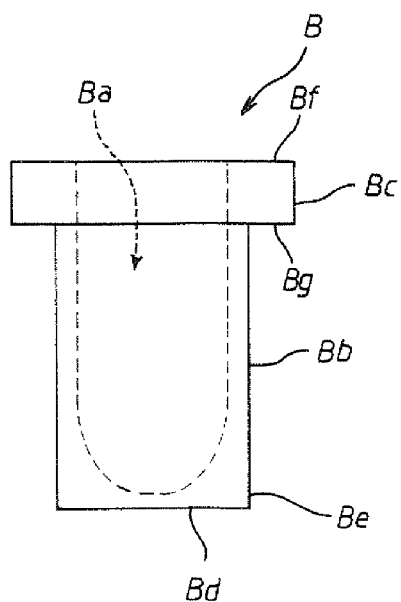
FIG. 3 is a front view illustrating a cylindrical container for sterilizing using the continuous sterilization system according to the first embodiment.

Here, the cylindrical container B is, as illustrated in FIG. 3, a cylindrical cup-shaped container in which an accommodating portion Ba for accommodating a pharmaceutical product is provided therein and is constituted by a cylindrical body portion Bb on an outside shape and a disk-shaped neck portion Bc provided above that and having an outer diameter larger than that.

Figure 4:
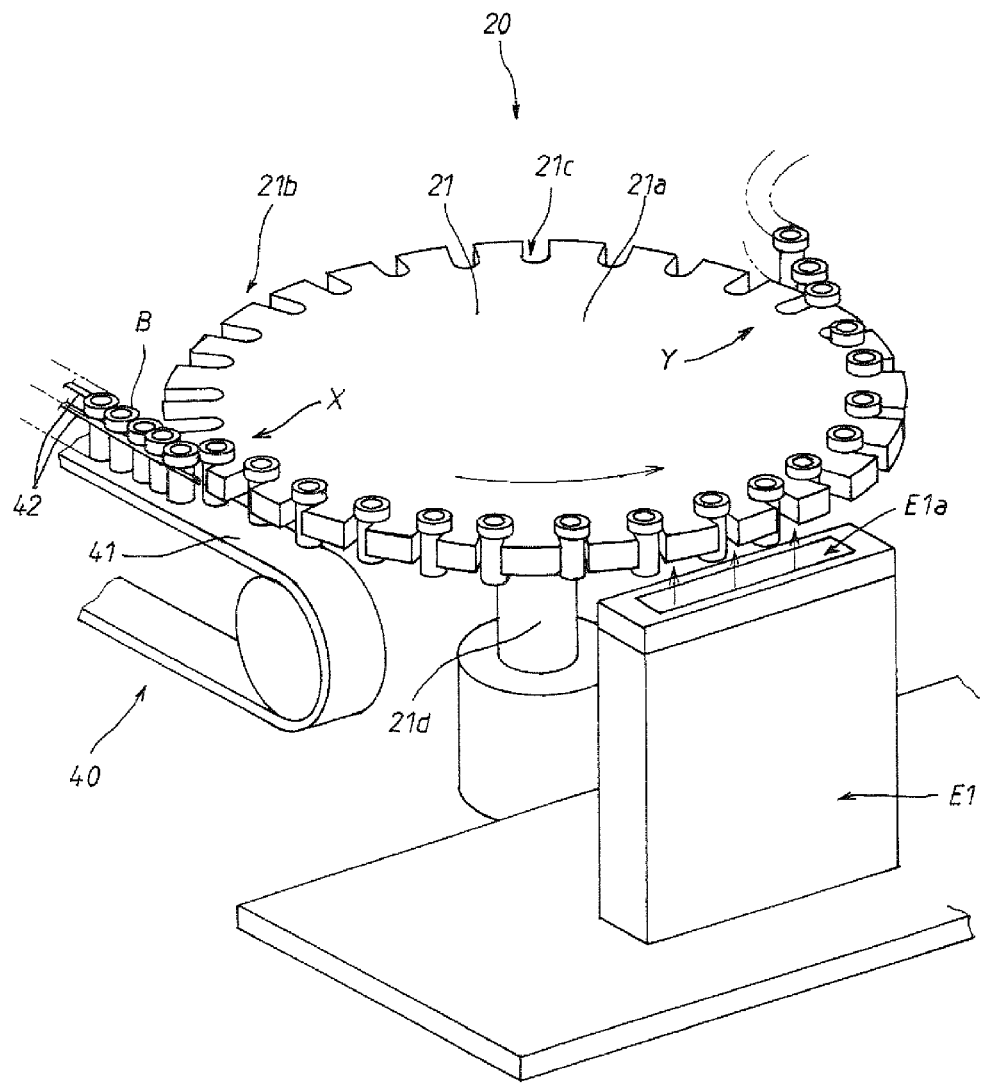
FIG. 4 is a perspective view illustrating a state in which electron beam irradiation by a first electron beam accelerator is emitted from the bottom surface portion side of a cylindrical container conveyed by a star-wheel conveyer mechanism in the continuous sterilization system according to the first embodiment.

The belt conveyer mechanism 40 has, as illustrated in FIG. 4, a belt conveyer 41 and two parallel guides 42. The belt conveyer 41 runs in a horizontal direction from the carrying-in port 11 and conveys the cylindrical containers B carried into the chamber 10 through the shutter 11a aligned on a single row in an upright state to the star-wheel conveyer mechanism 20.

Moreover, the two parallel guides 42 are arranged in a horizontal positional relationship with each other faced with a traveling direction of the belt conveyer 41, support the body portions Bb and the neck portions Bc of the cylindrical containers B aligned on a single row in the upright state from the both sides and assist the cylindrical containers B to move to the star-wheel conveyer mechanism 20 one by one without being tipped over.

The star-wheel conveyer mechanism 20 is, as illustrated in FIGS. 1 and 2, located on a left side portion (on the carrying-in port 11 side) of the chamber 10 and has a star wheel 21 and a rotary motor 22 (not shown) for rotating this star wheel 21 around a center axis of its disk face 21a.

The star wheel 21 is, as illustrated in FIG. 4, pivotally supported by the rotating shaft 21d extending upward from a bottom wall portion of the chamber 10 and is arranged with its disk face 21a arranged horizontally. On an outer edge portion 21b of this star wheel 21, a plurality of recess portions 21c are formed at equal intervals. This recess portion 21c supports the body portion Bb and carries the neck portion Bc of the cylindrical container B and conveys it along the outer edge portion 21b of the rotating star wheel 21. The rotary motor 22 (not shown) is located below the bottom wall portion of the chamber 10 and rotates the star wheel 21 through the rotating shaft 21d pivotally supporting the star wheel 21.

Figure 5:
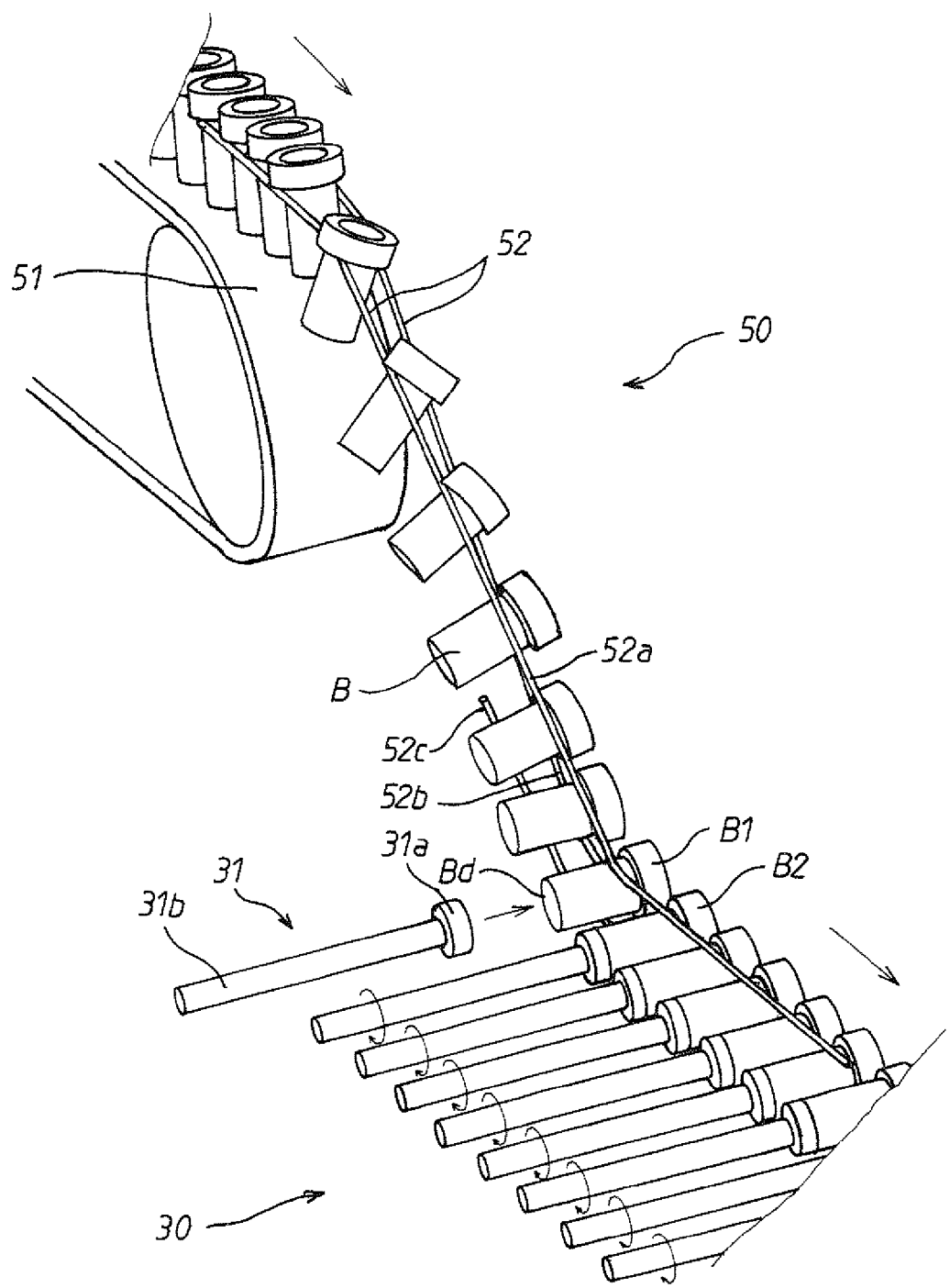
FIG. 5 is a perspective view illustrating a state in which the cylindrical container is reversed by a first spiral chute mechanism in the continuous sterilization system according to the first embodiment.

The spiral chute mechanism 50 has, as illustrated in FIG. 5, a belt conveyer 51 and two parallel guides 52. The belt conveyer 51 runs in the horizontal direction, receives the cylindrical containers B supported by the recess portions 21c of the star wheel 21 in the upright state (this portion is not shown), and conveys them aligned in a single row in the vicinity of the adsorption conveyer mechanism 30. Here, the belt conveyer 51 is located at a position higher than the position of the adsorption conveyer mechanism 30 (See FIG. 2), and the two parallel guides 52 are arranged between the belt conveyer 51 and the adsorption conveyer mechanism 30.

One end portions of the two parallel guides 52 are, as illustrated in FIG. 5, arranged in a horizontal positional relationship with each other faced with a traveling direction of the belt conveyer 51. As a result, one end portions of the two parallel guides 52 support the body portions Bb and the neck portions Bc of the cylindrical containers B aligned in a single row in the upright state from the both sides and assist conveyance of the cylindrical containers B to the end portion in the traveling direction of the belt conveyer 51.

As described above, the one end portions of the two parallel guides 52 are, as illustrated in FIG. 5, arranged in the horizontal positional relationship with each other at the position of the belt conveyer 51 but center parts of these two parallel guides 52 are spirally rotated so as to reverse the positional relationship with each other by approximately 90 degrees while being gradually inclined downward and moves to the height of the adsorption conveyer mechanism 30. In such a state, the center parts of the two parallel guides 52 support the body portions Bb and the neck portions Bc of the cylindrical containers B from the both sides and assist conveyance of the cylindrical containers B so that the upright state is reversed by approximately 90 degrees to a laterally directed state.

Moreover, the other end portions of the two parallel guides 52 are, as illustrated in FIG. 5, arranged in a positional relationship perpendicular to each other (52a on the upper side and 52b on the lower side) faced with the traveling direction of the adsorption conveyer mechanism 30. As a result, the other end portions of the two parallel guides 52 support the body portions Bb and the neck portions Bc of the cylindrical containers B reversed from the upright state by approximately 90 degrees to the laterally directed state from the both sides and assist conveyance of the cylindrical conveyers B to the position of the adsorption conveyer mechanism 30.

Furthermore, below the laterally directed cylindrical conveyers B, one auxiliary guide 52c is arranged in a horizontal positional relationship with one guide 52b (lower guide) of the parallel guides 52. As a result, the laterally directed state of the cylindrical containers B is made more stable by the two guides 52b and 52c in the horizontal positional relationship, and delivery to the subsequent adsorption conveyer mechanism 30 is facilitated.

Furthermore, though not shown, a screw conveyer or the like may be arranged at this delivery portion so that the delivery from the spiral chute mechanism 50 to the adsorption conveyer mechanism 30 can be made more accurately.

The adsorption conveyer mechanism 30 is, as illustrated in FIGS. 1 and 2, located at the center part of the chamber 10 and has a plurality of vacuum suction devices 31, a circularly moving conveyer 33 (which will be described later) for circularly moving the vacuum suction devices 31, and a rotary motor 32 (not shown) for driving the circularly moving conveyer 33 and rotating the vacuum suction devices 31.

Figure 6:
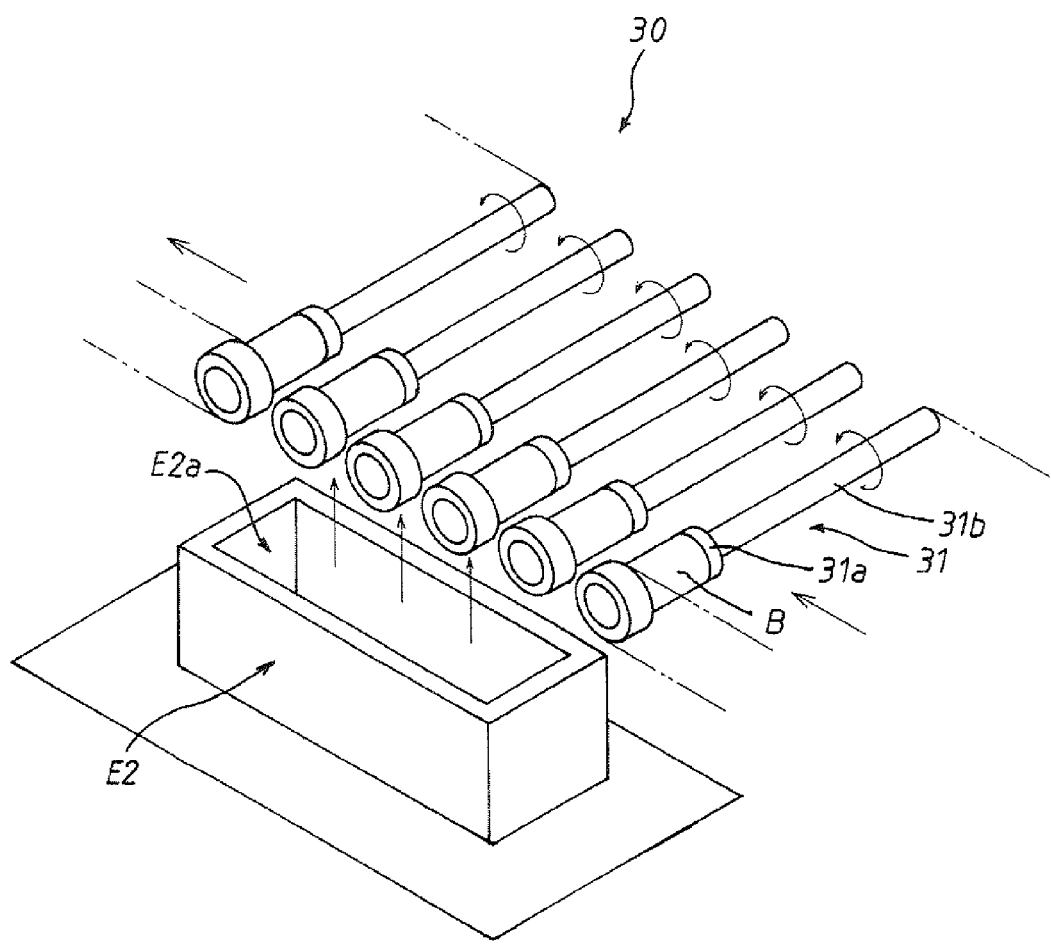
FIG. 6 is a perspective view illustrating a state in which electron beam irradiation by a second electron beam accelerator is emitted from the side surface portion side of the cylindrical container conveyed by an adsorption conveyer mechanism in the continuous sterilization system according to the first embodiment.
Figure 7:
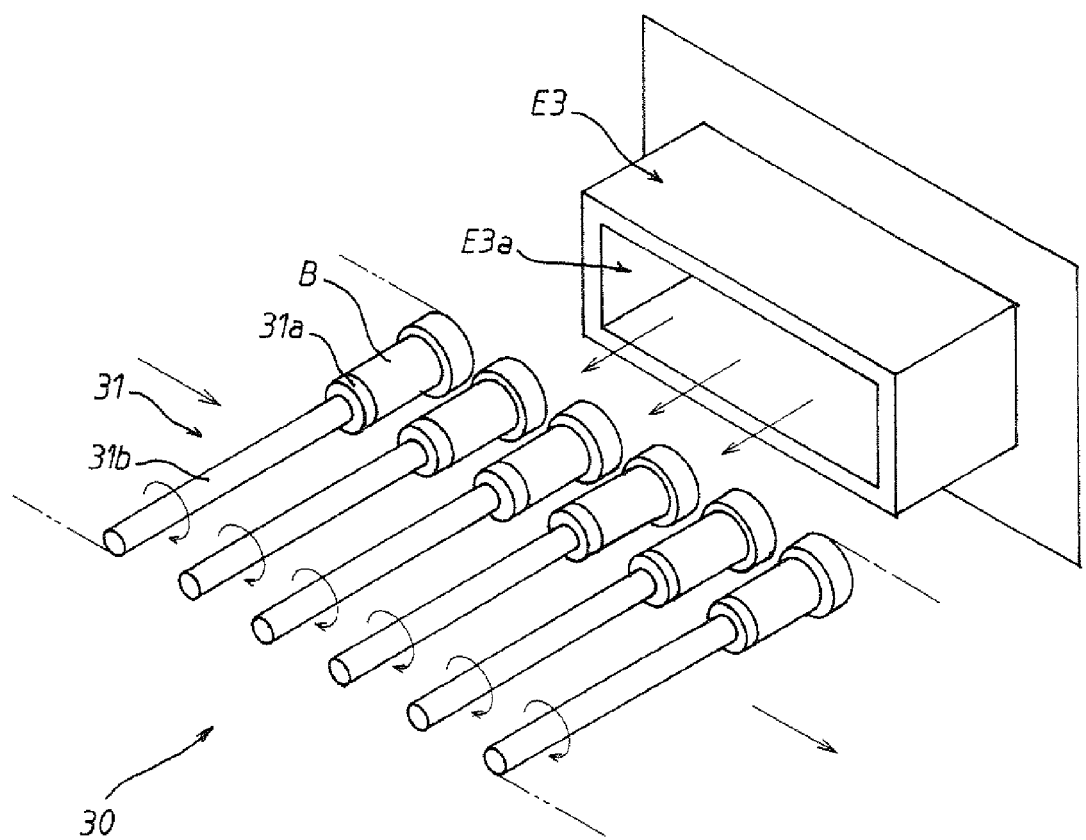
FIG. 7 is a perspective view illustrating a state in which electron beam irradiation by a third electron beam accelerator is emitted toward an inner surface portion of the cylindrical container conveyed by the adsorption conveyer mechanism in the continuous sterilization system according to the first embodiment.

Each of the plurality of vacuum suction devices 31 has, as illustrated in FIGS. 6 and 7, a cylindrical vacuum suction port 31a for suctioning and fixing a bottom portion Bd of the cylindrical container B and a suction tube 31b for pivotally supporting this vacuum suction port 31a along a cylindrical shaft of this vacuum suction port 31a, respectively. This vacuum suction device 31 is connected to a vacuum pump (not shown) through the suction tube 31b and transmits vacuum-suctioning by the vacuum pump to the vacuum suction port 31a through the suction tube 31b.

These vacuum suction devices 31 are provided in parallel with each other in a direction orthogonal to the conveying direction of the cylindrical containers B with the vacuum suction ports 31a and the cylindrical shafts of the suction tubes 31b directed horizontally (See FIGS. 6 and 7).

Figure 8:
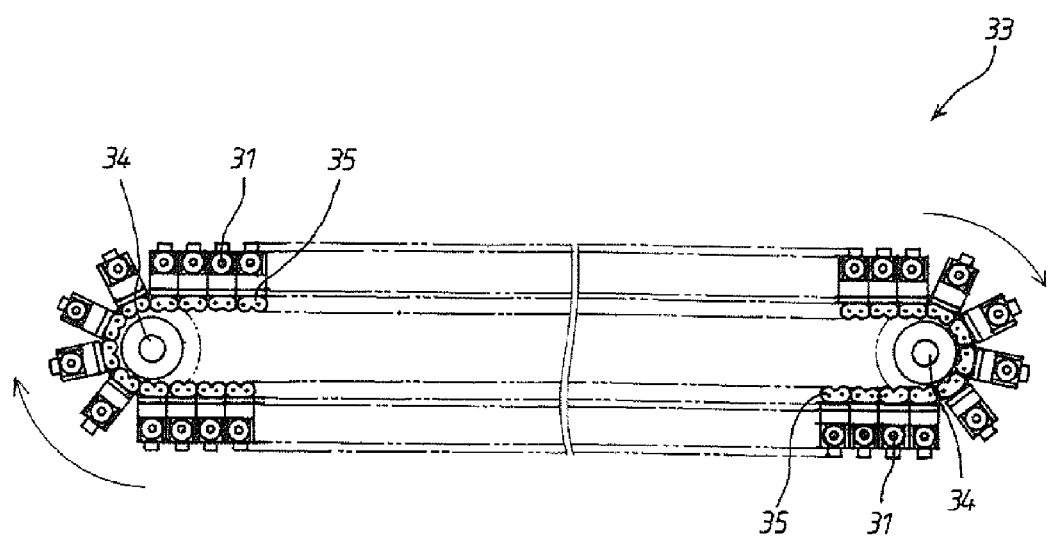
FIG. 8 is a front view illustrating an outline of a circularly moving conveyer of the adsorption conveyer mechanism in the continuous sterilization system according to the first embodiment.

The circularly moving conveyer 33 is provided with, as illustrated in an outline diagram when seen from its front in FIG. 8, four sprockets 34 (only right front and rear sides are shown) provided at four spots on right and left front and rear and both right and left chain belts 35 (only the right side is shown) wound around these sprockets. These chain belts 35 support the plurality of vacuum suction devices 31 on their outer peripheral sides. In this state, if the both right and left chain belts 35 rotate in a clockwise direction as illustrated through the sprockets 34 under driving of the rotary motor 32 (not shown), each of the vacuum suction devices 31 is circularly moved in two stages of upper and lower sides in conjunction with that.

Specifically, in FIG. 8, the plurality of vacuum suction devices 31 are arranged in two stages of upper and lower sides through the chain belts 35 of the circularly moving conveyer 33, in which the vacuum suction devices 31 on the upper stage move in the conveying direction (right side in the figure) of the cylindrical container B and descend to the lower stage and then, move in a direction (left side in the figure) opposite to the conveying direction of the cylindrical container B on the lower stage and ascend to the upper stage. As described above, the vacuum suction devices 31 convey the cylindrical container B from the left side in the figure to the right side in the figure on this upper stage while repeating circular movement on the two stages of upper and lower sides by means of driving of the circularly moving conveyer 33.

The rotary motor 32 rotates the circularly moving conveyer 33 as described above, though not shown, and drives the vacuum suction port 31a and the suction tube 31b pivotally supporting this vacuum suction port 31a along its cylindrical shaft so that they rotate around their cylindrical shafts. A mechanism for transmitting the driving of this rotary motor 32 to each of the suction tubes 31b and the vacuum suction ports 31a can be of any type and it may be gear driving or belt driving, for example. The vacuum suction port 31a and the suction tube 31b are fixedly connected, while connection between the suction tube 31b and the vacuum pump is preferably made by a mechanical seal or the like, for example, so that rotation of the suction tube 31b is made possible.

Figure 9:
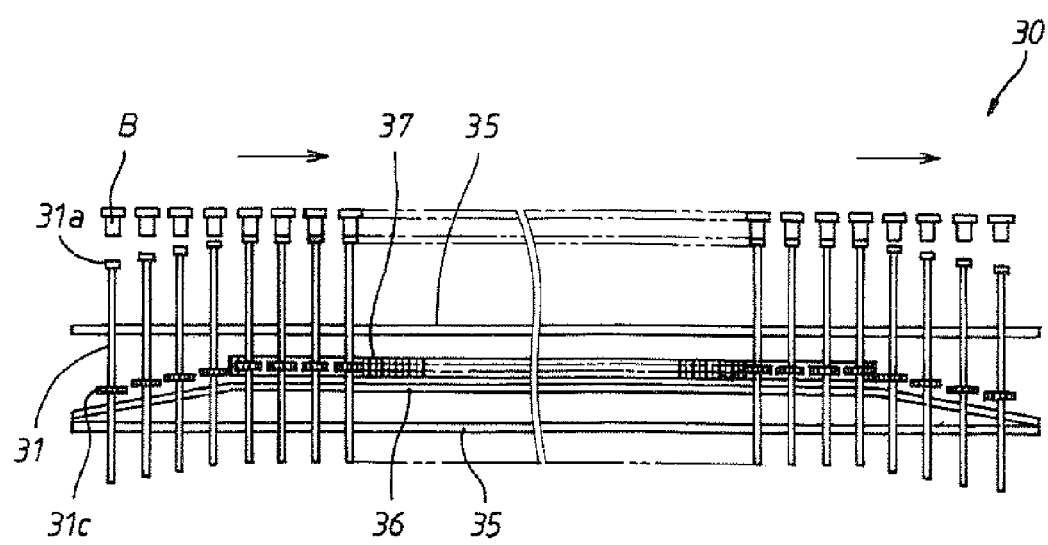
FIG. 9 is a plan view illustrating a state in which a vacuum suction device 31 of the adsorption conveyer mechanism moves by the circularly moving conveyer in the continuous sterilization system according to the first embodiment.

Here, a mechanism in which the adsorption conveyer mechanism 30 receives the cylindrical container B from the spiral chute mechanism 50 suctions and fixes it and conveys it and delivers it to the subsequent spiral chute mechanism 60 will be described by using a figure. FIG. 9 is an outline diagram of the adsorption conveyer mechanism 30 when seen from the upper stage side. The adsorption conveyer mechanism 30 disposes the plurality of vacuum suction devices 31 with their cylindrical shafts directed horizontally and in parallel with each other in a direction orthogonal to the conveying direction (right side in the figure) of the cylindrical container B.

These vacuum suction devices 31 are supported slidably in their cylindrical shaft directions, respectively, on the chain belts 35 of the circularly moving conveyer 33 as described above, and each of these vacuum suction devices 31 is coaxially provided with a pinion gear 31c at the center part of its suction tube 31b, respectively.

Moreover, in FIG. 9, the adsorption conveyer mechanism 30 is provided with a slide guide 36 for supporting and slidingly moving the vacuum suction devices 31 in a direction (vertical direction in the figure) orthogonal to the traveling direction and a rack gear 37 meshed with the pinion gear 31c provided in the vacuum suction device 31 and rotating the vacuum suction device 31.

In FIG. 9, the cylindrical container B moves from the spiral chute mechanism 50 (not shown) to the right in the figure and reaches an introduction portion (left end in the figure) of the adsorption conveyer mechanism 30. At this point, the vacuum suction port 31a of the vacuum suction device 31 is located at a position away from the cylindrical container B and does not suction or fix the cylindrical container B.

Subsequently, the vacuum suction device 31 slides along the slide guide 36 while moving to the right in the figure with the driving of the circularly moving conveyer 33 and gets close to the cylindrical container B and suctions and fixes the cylindrical container B with the vacuum suction port 31a.

At this position, the pinion gear 31c of the vacuum suction device 31 is meshed with the rack gear 37. After that, with driving of the circularly moving conveyer 33, the vacuum suction device 31 moves to the right side in the figure, whereby the pinion gear 31c moves on the rack gear 37 while rotating. As a result, the vacuum suction device 31 rotates, and the cylindrical container B suctioned and fixed by that rotates along its cylindrical shaft.

Subsequently, the vacuum suction device 31 further moves to the right in the figure with the driving of the circularly moving conveyer 33. After that, the vacuum suction device 31 releases the cylindrical container B from suctioning and fixation and also, the vacuum suction device 31 slides along the slide guide 36 while moving to the right in the figure with the driving of the circularly moving conveyer 33 and separates away from the cylindrical container B.

Figure 10:
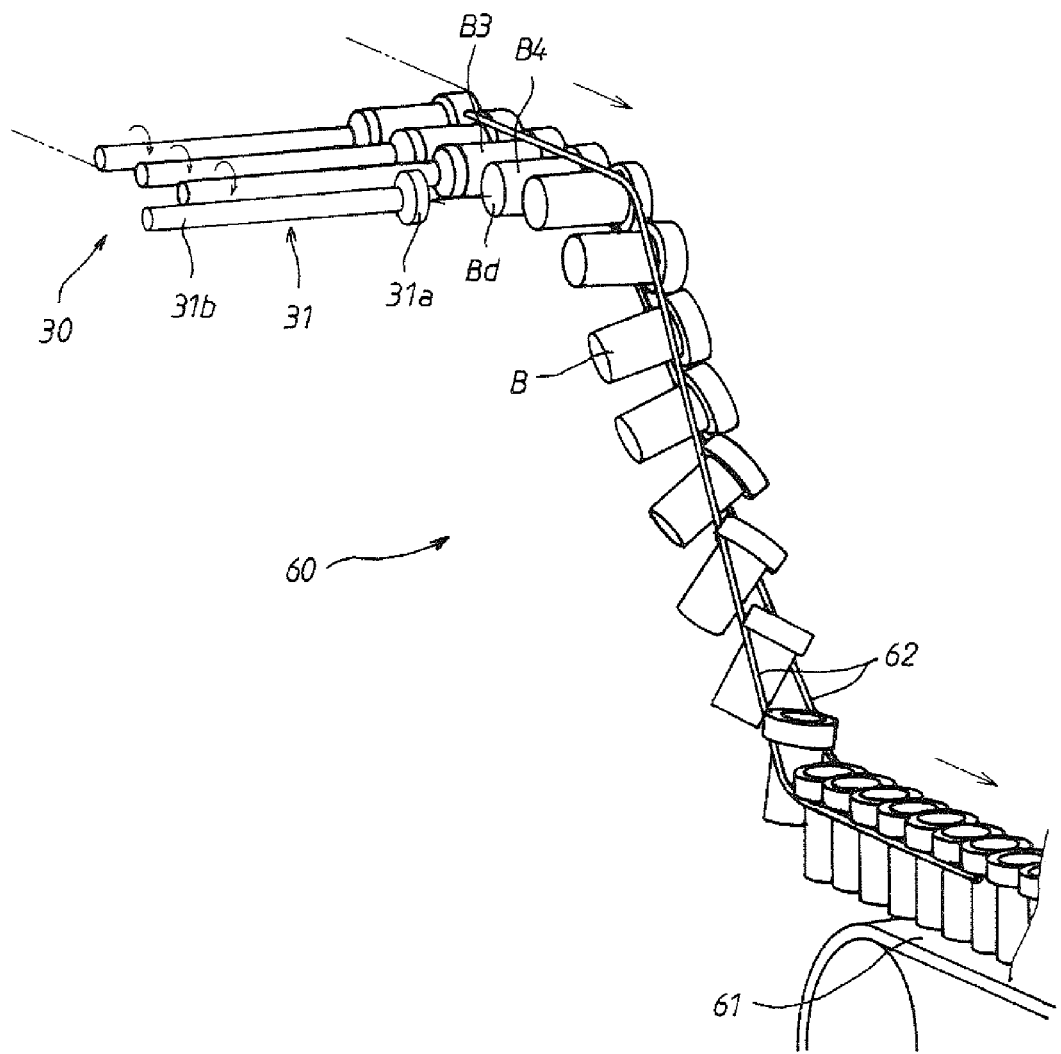
FIG. 10 is a perspective view illustrating a state in which the cylindrical container is reversed by a second spiral chute mechanism in the continuous sterilization system according to the first embodiment.

The spiral chute mechanism 60 has, as illustrated in FIG. 10, a belt conveyer 61 and two parallel guides 62. Here, the belt conveyer 61 is located at a position lower than the position of the adsorption conveyer mechanism 30 (See FIG. 2), and the two parallel guides 62 are arranged between the belt conveyer 61 and the adsorption conveyer mechanism 30.

One end portions of the two parallel guides 62 are, as illustrated in FIG. 10, arranged in the positional relationship perpendicular to each other faced with the traveling direction of the adsorption conveyer mechanism 30. As a result, the one end portions of the two parallel guides 62 support the body portions Bb and the neck portions Bc of the cylindrical containers B aligned in a single row in the laterally directed state from the both sides and assist conveyance of the cylindrical containers B to the end portion in the traveling direction of the adsorption conveyer mechanism 30.

As described above, the one end portions of the two parallel guides 62 are, as illustrated in FIG. 10, arranged in the positional relationship perpendicular to each other at the position of the adsorption conveyer mechanism 30, but the center parts of these two parallel guides 62 spirally rotate so as to reverse the positional relationship with each other by approximately 90 degrees while being gradually inclined downward and move to the height of the belt conveyer 61. In such a state, the center parts of the two parallel guides 62 support the body portions Bb and the neck portions Bc of the cylindrical containers B from the both sides and assist conveyance of the cylindrical containers B so that they are reversed by approximately 90 degrees from the laterally directed state to the upright state.

Moreover, the other end portions of the two parallel guides 62 are, as illustrated in FIG. 10, arranged in a horizontal positional relationship with each other faced with the traveling direction of the belt conveyer 61. As a result, the other end portions of the two parallel guides 62 support the body portions Bb and the neck portions Bc of the cylindrical containers B in the upright state from the laterally directed state by being reversed by approximately 90 degrees from the both sides and assist conveyance of the cylindrical containers B to the position of the belt conveyer 61.

Furthermore, the belt conveyer 61 conveys the cylindrical container B received from the adsorption conveyer mechanism 30 through the two parallel guides 62 to the belt conveyer mechanism 70. At this time, the two parallel guides 62 arranged in the horizontal positional relationship with each other faced with the traveling direction of the belt conveyer 61 support the body portions Bb and the neck portions Bc of the cylindrical containers B aligned in a single row in the upright state from the both sides and assist the cylindrical containers B to move to the belt conveyer mechanism 70 one by one without being tipped over.

The belt conveyer mechanism 70 has a plurality of belt conveyers and a plurality of guides, though not shown, and receives the cylindrical conveyer B from the belt conveyer 61 of the spiral chute mechanism 60 and conveys it to the carrying-out port 12 and carries it out through the shutter 12a and carries it into the aseptic workroom.

The electron beam accelerator E1 in the three electron beam accelerators E1, E2, and E3 is, as illustrated in FIGS. 1 and 2, located on the outside of the bottom wall portion on the left side part (on the carrying-in port 11 side) of the chamber 10. This electron beam accelerator E1 is, as illustrated in FIG. 4, located with an irradiation port E1a directed upward from the bottom wall portion of the chamber 10 and emits an electron beam toward the bottom portion Bd of the cylindrical container B supported by the recess portion 21c provided on the outer edge portion 21b of the star wheel 21. This emitted electron beam can sufficiently sterilize not only the bottom portion Bd of the cylindrical container B but also a lower portion Be of the body portion in the vicinity of the bottom portion Bd.

The electron beam accelerator E2 is, as illustrated in FIGS. 1 and 2, located on the outside of the bottom wall portion at the center part of the chamber 10. This electron beam accelerator E2 is, as illustrated in FIG. 6, located with an irradiation port E2a directed upward from the bottom wall portion of the chamber 10 and emits the electron beam toward the body portion Bb and the neck portion Bc of the cylindrical container B supported by the vacuum suction port 31a of the vacuum suction device 31 and sterilizes the portion. At this time, since the cylindrical container B supported by the vacuum suction port 31a rotates together with the vacuum suction device 31 around its cylindrical shaft, the cylindrical container B is sterilized over the entire periphery of its side surface. The irradiation of the electron beam from the irradiation port E2a can sufficiently sterilize not only the side surfaces of the body portion Bb and the neck portion Bc of the cylindrical container B but also an upper surface Bf and a lower surface Bg of the neck portion Bc.

The electron beam accelerator E3 is, as illustrated in FIGS. 1 and 2, located on the outside of a rear wall portion close to the right side of the center part of the chamber 10. This electron beam accelerator E3 is, as illustrated in FIG. 7, located with an irradiation port E3a directed from the rear wall portion of the chamber 10 toward the front side and emits the electron beam toward the upper surface Bf of the neck portion Bc of the cylindrical container B supported by the vacuum suction port 31a of the vacuum suction device 31 and the accommodating portion Ba and sterilizes the portion.

Here, particularly the accommodating portion Ba for accommodating pharmaceutical products can be sufficiently sterilized.

As these electron beam accelerators E1, E2, and E3, a small-sized or low-energy type may be used in general, and it may be a radiation source: 40 to 200 kV, 3.5 to 5 mA, for example.

Here, an operation of sterilizing the cylindrical container B using the continuous sterilization system 100 according to this first embodiment configured as above and of carrying this sterilized cylindrical container B into the aseptic workroom will be described.

In FIG. 1, the continuous sterilization system 100 and the aseptic workroom (not shown) installed consecutively to the side surface on the right side in the figure are both under the aseptic environment, and a filling work of pharmaceutical products is performed inside the aseptic workroom. At this time, the shutters 11a and 12a of the carrying-in port 11 and the carrying-out port 12 of the continuous sterilization system 100 are opened, the cylindrical containers B before sterilization are continuously carried into the continuous sterilization system 100, and the cylindrical containers B sterilized in the continuous sterilization system 100 are continuously carried into the aseptic workroom.

In such a state, the cylindrical container B carried into the continuous sterilization system 100 from the outside environment is first conveyed by the belt conveyer 41 of the belt conveyer mechanism 40 to a receiving position X of the star wheel 21 of the star-wheel conveyer mechanism 20 (See FIG. 1) aligned in a single row in the upright state.

Subsequently, the cylindrical container B is, as illustrated in FIG. 4, supported in the upright state by the star wheel 21 rotating counterclockwise in the figure through the rotating shaft 21d (X position in FIG. 4). Specifically, the cylindrical container B is supported one by one by the recess portion 21c provided at equal intervals on the outer edge portion 21b of the star wheel 21 on its body portion Bb and the neck portion Bc. At this time, outer surfaces of the bottom portion Bd of the cylindrical container B and the lower portion Be of the body portion in the vicinity thereof are not in contact with the recess portion 21c of the star wheel 21.

As described above, the cylindrical containers B supported at equal intervals by the outer edge portion 21b of the star wheel 21 are conveyed to an upper position of the irradiation port E1a of the electron beam accelerator E1 counterclockwise in the figure along the outer edge portion 21b of the star wheel 21 (See FIG. 4). Here, the outer surfaces of the bottom portion Bd of the cylindrical container B being conveyed and the lower portion Be of the body portion in the vicinity thereof are sterilized by the electron beam emitted from the irradiation port E1a of the electron beam accelerator E1. At this time, by controlling the rotation speed of the star wheel 21, an opening diameter of the irradiation port E1a, and electron beam strength, the outer surfaces of the bottom portion Bd of the cylindrical container B and the lower portion Be of the body portion in the vicinity thereof are fully sterilized.

Subsequently, the cylindrical container B in which the outer surfaces of the bottom portion Bd and the lower portion Be of the body portion in the vicinity thereof have been sterilized is further conveyed counterclockwise in the figure along the outer edge portion 21b of the star wheel 21 and conveyed to a delivery position Y. At this delivery position Y, the belt conveyer 51 of the spiral chute mechanism 50 (not shown in FIG. 4) is arranged, and the cylindrical container B having been conveyed to the delivery position Y is guided by the guide (not shown) and received in the upright state on the belt conveyer 51 and aligned in a single row in the traveling direction of the belt conveyer 51.

The belt of the belt conveyer 51 has been fully sterilized in advance, and even if the bottom portion Bd of the cylindrical container B having been sterilized by electron beam irradiation from the electron beam accelerator E1 is brought into contact, this bottom portion Bd is not contaminated again.

Subsequently, the cylindrical container B is conveyed on the belt conveyer 51 and reaches an end portion in the traveling direction of the belt conveyer 51 (See FIG. 5). Below the end portion in the traveling direction of the belt conveyer 51, the adsorption conveyer mechanism 30 is arranged, and the two parallel guides 52 of the spiral chute mechanism 50 connect the belt conveyer 51 and the adsorption conveyer mechanism 30 to each other.

The cylindrical containers B having been conveyed by the belt conveyer 51 in a single row in the upright state are, as illustrated in FIG. 5, supported on the body portion Bb and the neck portion Bc by the two parallel guides 52 arranged in the horizontal positional relationship on the end portion in the traveling direction of the belt conveyer 51 from the both sides and in the upright state. At this time, the outer surfaces of the bottom portion Bd of the cylindrical container B and the lower portion Be of the body portion in the vicinity thereof are kept in the state sterilized by the previous electron beam irradiation by the electron beam accelerator E1.

Subsequently, the cylindrical container B separates away from the end portion in the traveling direction of the belt conveyer 51 and spirally drops while being gradually inclined downward, assisted by the two parallel guides 52. At this time, the cylindrical container B is reversed from the upright state by approximately 90 degrees to the laterally directed state and moves to the height of the adsorption conveyer mechanism 30.

In this state, the cylindrical container B is, as illustrated in FIG. 5, supported on the body portion Bb and the neck portion Bc from the both sides by the two parallel guides (52*a*, 52*b*) arranged in the perpendicular positional relationship with each other in the laterally directed state after being reversed by approximately 90 degrees from the upright state. Moreover, the cylindrical container B is supported more stably in the laterally directed state by the auxiliary guide 52*c* arranged in the horizontal positional relationship with the one parallel guide 52*b*.

Subsequently, the cylindrical container B having reached the adsorption conveyer mechanism 30 (a state of B1 in FIG. 5) is supported by the vacuum suction device 31 on its bottom portion Bd (a state of B2 in FIG. 5). That is, as described above, the vacuum suction device 31 approaches the cylindrical container B from its bottom portion Bd side, brings the vacuum suction port 31*a* into contact with the bottom portion Bd and supports it by vacuum-suctioning. A suctioning force of this vacuum suction port 31*a* is, as described above, realized by a vacuum pump (not shown) connected through the suction tube 31*b*.

The vacuum suction port 31*a* of the vacuum suction device 31 is fully sterilized in advance, and even if the bottom portion Bd of the cylindrical container B having been sterilized by the electron beam irradiation from the electron beam accelerator E1 is vacuum-suctioned by the vacuum suction port 31*a*, this bottom portion Bd is not contaminated again.

As described above, the cylindrical container B vacuum-suctioned by the vacuum suction device 31 on its bottom portion Bd and supported is rotated by driving of the rotary motor 32 together with the vacuum suction port 31*a* and the suction tube 31*b* around their cylindrical shafts as described above. Moreover, this cylindrical container B is circularly moved by driving of the circularly moving conveyer 33 in the conveying direction as described above.

Subsequently, the cylindrical container B supported by the vacuum suction device 31 is conveyed to the upper position of the irradiation port E2*a* of the electron beam accelerator E2 while rotating together with the vacuum suction port 31*a* and the suction tube 31*b* around these cylindrical shafts (See FIG. 6). Here, the outer surfaces of the body portion Bb and the neck portion Bc of the cylindrical container B being conveyed are sterilized by the electron beam emitted from the irradiation port E2*a* of the electron beam accelerator E2.

Here, since the cylindrical container B is rotating together with the vacuum suction device 31 around its cylindrical shaft, this cylindrical container B is sterilized over the entire periphery of its side surface. At this time, by controlling the rotating speed and circularly moving speed of the vacuum suction device 31, the opening diameter of the irradiation port E2*a*, and the electron beam strength, the outer surfaces of the body portion Bb and the neck portion Bc of the cylindrical container B are fully sterilized.

Subsequently, the cylindrical container B supported by the vacuum suction device 31 is conveyed to the front position of the irradiation port E3*a* of the electron beam accelerator E3 (See FIG. 7). Here, the upper surface Bf of the neck portion Bc and an inner surface of the accommodating portion Ba of the cylindrical container B being conveyed are sterilized by the electron beam emitted from the irradiation port E3*a* of the electron beam accelerator E3. At this time, by controlling the circularly moving speed of the vacuum suction device 31, the opening diameter of the irradiation port E3*a*, and the electron beam strength, the upper surface Bf of the neck portion Bc and an inner surface of the accommodating portion Ba of the cylindrical container B are fully sterilized.

As described above, in the cylindrical container B, its bottom portion Bd, the body portion Bb, and the neck portion Bc as well as the upper surface Bf of the neck portion Bc and the entire inner and outer surfaces of the accommodating portion Ba of the cylindrical container B are fully sterilized.

Subsequently, the cylindrical container B having the entire inner and outer surfaces fully sterilized and having reached the end portion in the traveling direction of the adsorption conveyer mechanism 30 is supported by the vacuum suction device 31 on its bottom portion Bd (state of B3 in FIG. 10). Here, as described above, the vacuum suction device 31 releases the bottom portion Bd of the cylindrical container B from vacuum suctioning and also separates away from the bottom portion Bd side (state of B4 in FIG. 10). At this time, the cylindrical container B is supported on the body portion Bb and the neck portion Bc from the both sides by the two parallel guides 62 arranged in the perpendicular positional relationship with each other still in the laterally directed state.

The two parallel guides 62 have been fully sterilized in advance, and even if they are brought into contact with the body portion Bb and the neck portion Bc of the cylindrical container B having its entire inner and outer surfaces sterilized by the electron beam irradiation of the electron beam accelerator E1 to E3, this portion is not contaminated again.

Subsequently, the cylindrical container B is reversed from the laterally directed state by approximately 90 degrees to the upright state and moved to the height of the belt conveyer 61 while being assisted by the two parallel guides 62 and gradually dropping downward spirally. In this state, the cylindrical containers B are, as illustrated in FIG. 10, reversed from the laterally directed state by approximately 90 degrees to the upright state and supported on the body portion Bb and the neck portion Bc from the both sides by the two parallel guides 62 arranged in the horizontal positional relationship and are aligned in a single row in the traveling direction of the belt conveyer 61.

The belt of the belt conveyer 61 has been fully sterilized in advance, and even if the bottom portion Bd of the cylindrical container B whose entire inner and outer surfaces have been sterilized by electron beam irradiation of the electron beam accelerators E1 to E3 is brought into contact, this bottom portion Bd is not contaminated again.

Subsequently, the cylindrical containers B are conveyed by the belt conveyer 61 to the position of the belt conveyer mechanism 70, though not particularly illustrated, and after that, aligned in a single row still in the upright state and conveyed to the carrying-out port 12 while changing their traveling direction by the plurality of belt conveyers and guides (none of them is illustrated) of the belt conveyer mechanism 70 and carried into the aseptic workroom through the shutter 12*a* (See FIGS. 1 and 2).

Second Embodiment

Subsequently, a second embodiment of a continuous sterilization system according to the present invention will be described in accordance with the attached drawings. The continuous sterilization system 200 according to the second embodiment has a structure similar to that of the first embodiment except that the adsorption conveyer mechanism 30 in the first embodiment is changed to a chucking conveyer mechanism 130 (See FIGS. 1, 2, and 4). Moreover, a sterilization target to be sterilized by the continuous sterilization system according to the second embodiment is also the cylindrical container B having the structure similar to that of the first embodiment (See FIG. 3).

That is, inside the chamber 10, the star-wheel conveyer mechanism 20 and the chucking conveyer mechanism 130 for supporting and conveying the cylindrical container B in order to emit the electron beam as well as the three electron beam accelerators E1, E2, and E3 for irradiating the electron beam to each portion of the cylindrical container B being conveyed by them for sterilization are provided.

Moreover, inside the chamber 10, the belt conveyer mechanism 40 for conveying the cylindrical container B from the carrying-in port 11 to the star-wheel conveyer mechanism 20, the spiral chute mechanism 50 for delivery from the star-wheel conveyer mechanism 20 to the chucking conveyer mechanism 130, the spiral chute mechanism 60 for receiving the cylindrical container B from the chucking conveyer mechanism 130, and the belt conveyer mechanism 70 for receiving the cylindrical container B from this spiral chute mechanism 60 and conveying it to the carrying-out port 12 are provided.

In this second embodiment, the chucking conveyer mechanism 130 is located at the center part of the chamber 10 similarly to the adsorption conveyer mechanism 30 in the first embodiment (See FIGS. 1 and 2) and has a plurality of chucking devices 131, a circularly moving conveyer 133 (which will be described later) for circularly moving the chucking device 131, and a rotary motor 32 (not shown) for driving the circularly moving conveyer 133 and rotating the chucking device 131.

Figure 11:
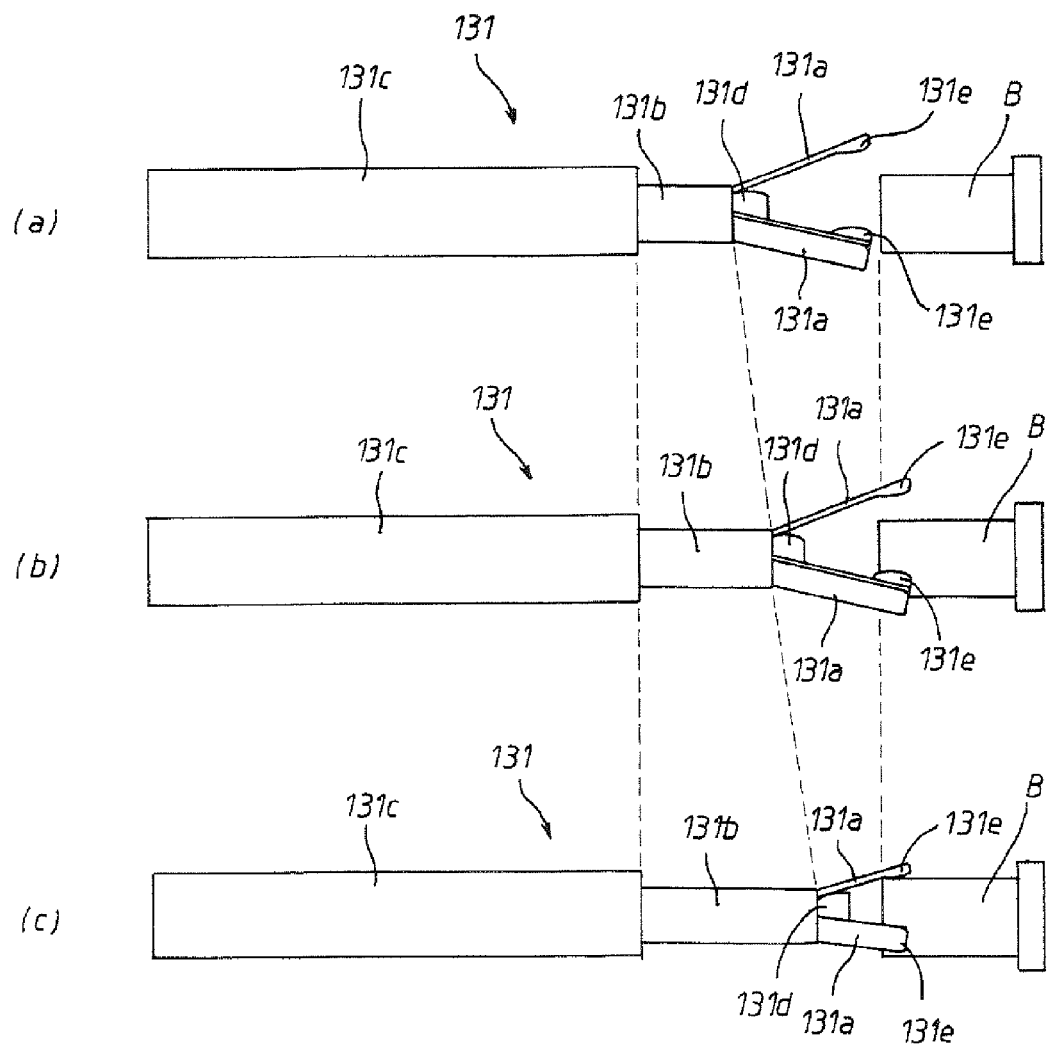
FIG. 11 is an outline diagram illustrating a state in which a chucking member chucks the cylindrical container in a continuous sterilization system according to a second embodiment.

Each of the plurality of chucking devices 131 has, as illustrated in FIG. 11, three claws 131*a* for chucking and fixing the lower portion Be of the body portion in the vicinity of the bottom portion Bd of the cylindrical container B, an inner cylindrical tube 131*b* supporting these three claws 131*a*, and an outer cylindrical tube 131*c* pivotally supporting this inner cylindrical tube 131*b* from an outer periphery portion, respectively.

The three claws 131*a* are disposed at positions in three equally divided parts in the tube circumferential direction from one end portion (open portion) of the inner cylindrical tube 131*b*, respectively, and extend so as to expand outward from the extending direction of one end portion of the inner cylindrical tube 131*b*. In FIG. 11, a state in which two of the three claws 131*a* are overlapped and only two of them are seen is illustrated. An open state of these three claws 131*a* is fixed from the inside by a pressing element 131*d* provided on the one end portion of the inner cylindrical tube 131*b*. Moreover, the other end portion of the inner cylindrical tube 131*b* is internally inserted slidably in the tube axial direction into the outer cylindrical tube 131*c*.

Here, a state in which the chucking device 131 chucks the lower portion Be of the body portion of the cylindrical container B will be described in accordance with FIG. 11. FIG. 11(*a*) illustrates the chucking device 131 before chucking the cylindrical container B. Here, the three claws 131*a* are widely open outward in the extending direction from the one end portion of the inner cylindrical tube 131*b*, and each of distal end portions 131*e* of the three claws 131*a* is open more widely than an outer diameter of the lower portion Be of the body portion of the cylindrical container B. Moreover, the other end portion of the inner cylindrical tube 131*b* is in a state largely inserted into the outer cylindrical tube 131*c*, and a position of each of the distal end portions 131*e* of the three claws 131*a* is located at a position separated from the lower portion Be of the body portion of the cylindrical container B.

Subsequently, the chucking device 131 is changed from the state in FIG. 11(*a*) to the state in FIG. 11(*b*). Here, the open state of the three claws 131*a* extending from the one end portion of the inner cylindrical tube 131*b* has not been changed, and each of the distal end portions 131*e* of the three claws 131*a* is opened more widely than the outer diameter of the lower portion Be of the body portion of the cylindrical container B. On the other hand, the inner cylindrical tube 131*b* is in a state largely pulled out from the inside of the outer cylindrical tube 131*c* in the right direction in the figure, and as a result, the position of each of the distal end portions 131*e* of the three claws 131*a* is close to a position holding the lower portion Be of the body portion of the cylindrical container B.

Subsequently, the chucking device 131 changes from the state in FIG. 11(*b*) to the state in FIG. 11(*c*). Here, the inner cylindrical tube 131*b* is in the state further largely pulled out than the state in FIG. 11(*b*) in the right direction in the figure from the inside of the outer cylindrical tube 131*c*. At this time, since pressing by the pressing element 131*d* onto the one end portion of the inner cylindrical tube 131*b* is loosened, the open state of the three claws 131*a* is closed, and a base end portion of each claw 131*a* enters a state inserted into the inner cylindrical tube 131*b*. As a result, each of the distal end portions 131*e* of the three claws 131*a* is closed, and each of the distal end portions 131*e* of the three claws 131*a* chucks the lower portion Be of the body portion of the cylindrical container B so that the cylindrical container B is reliably supported by the chucking devices 131.

If the chucking devices 131 release chucking of the cylindrical container B, a process opposite to the above is performed, that is, the state in FIG. 11(*c*) is changed to the state in FIG. 11(*b*) and moreover, the state in FIG. 11(*b*) is changed to the state in FIG. 11(*a*).

Figure 13:
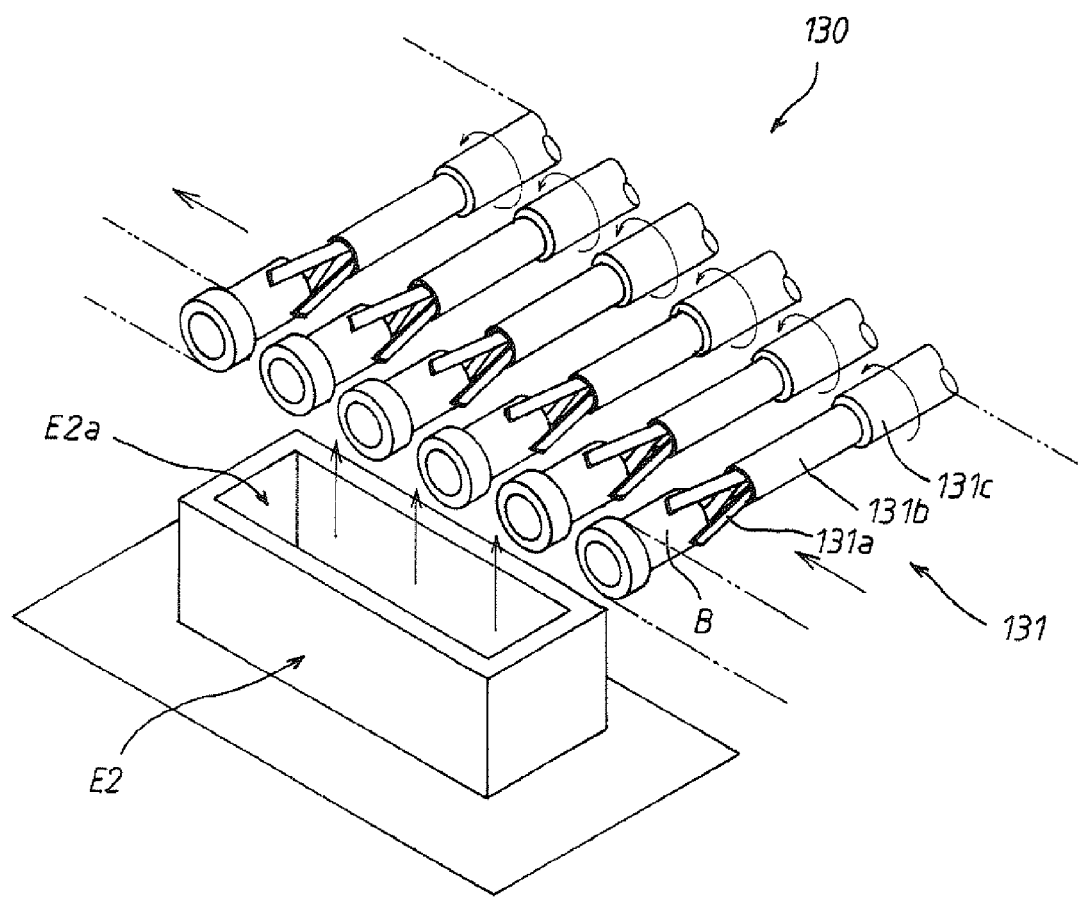
FIG. 13 is a perspective view illustrating a state in which electron beam irradiation by a second electron beam accelerator is emitted from the side surface portion side of the cylindrical container conveyed by the adsorption conveyer mechanism in the continuous sterilization system according to the second embodiment.
Figure 14:
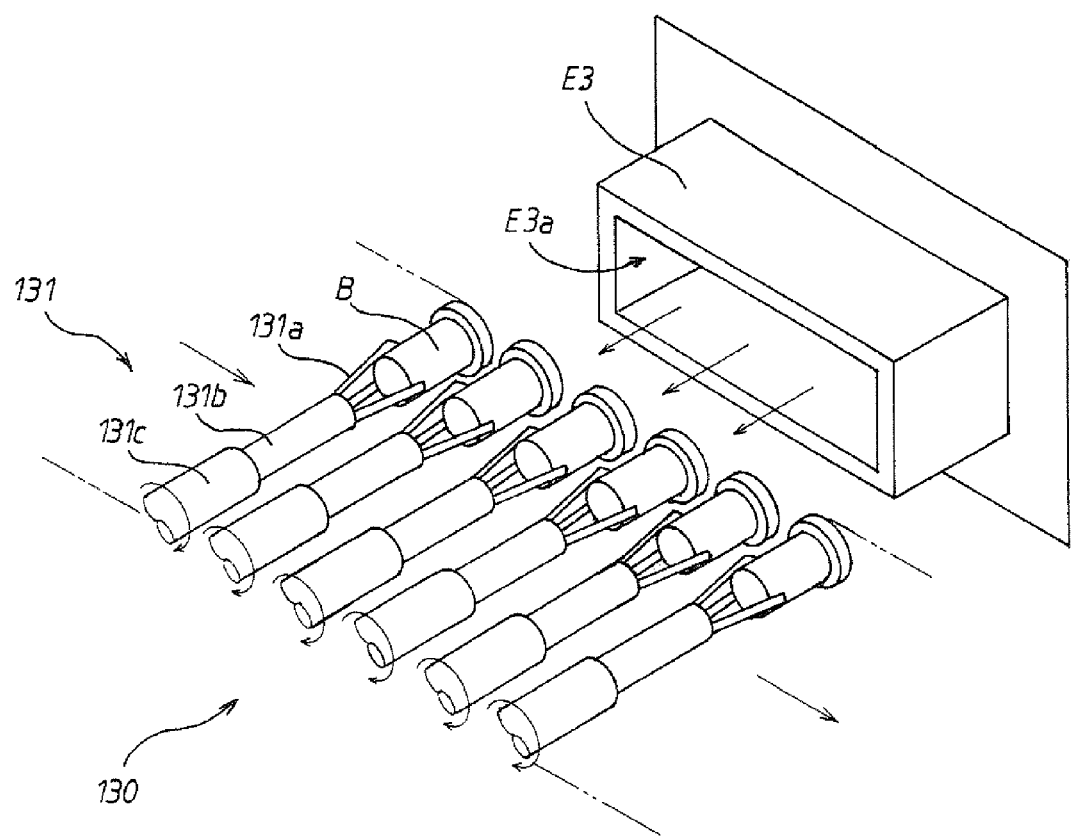
FIG. 14 is a perspective view illustrating a state in which electron beam irradiation by a third electron beam accelerator is emitted toward an inner surface portion of the cylindrical container conveyed by the adsorption conveyer mechanism in the continuous sterilization system according to the second embodiment.

These chucking devices 131 are provided in parallel with each other in a direction orthogonal to the conveying direction of the cylindrical container B with tube shafts of the inner cylindrical tube 131b and the outer cylindrical tube 131c horizontally directed (See FIGS. 13 and 14).

The circularly moving conveyer 133 has the configuration and driving mechanism similar to those in the first embodiment except that the vacuum suction device 31 in the first embodiment is replaced by the chucking device 131 (See FIG. 8), and this chucking device 131 conveys the cylindrical container B on the upper stage from the left side to the right side in the figure while repeating circular movement in the two upper and lower stages by driving of the circularly moving conveyer 133.

The rotary motor 32 rotates the circularly moving conveyer 33 as described above, though not shown, and drives the vacuum suction port 31a and the suction tube 31b pivotally supporting this vacuum suction port 31 along its cylindrical shaft so that they rotate around their cylindrical shafts. A mechanism for transmitting the driving of this rotary motor 32 to each of the suction tubes 31b and the vacuum suction port 31a may be of any type and may be gear driving or belt driving, for example. The vacuum suction port 31a and the suction tube 31b are fixedly connected, while connection between the suction tube 31b and the vacuum pump is preferably made by mechanical seal or the like, for example, so that rotation of the suction tube 31b is made possible.

The rotary motor 132 rotates the circularly moving conveyer 133 as described above and also drives the inner cylindrical tube 131b and the outer cylindrical tube 131c so that they rotate around their tube axes, though not shown. A mechanism for transmitting the driving of this rotary motor 132 to each of the inner cylindrical tube 131b and the outer cylindrical tube 131c may be of any type similarly to the first embodiment. The inner cylindrical tube 131b and the outer cylindrical tube 131c are slidably inserted internally as described above but rotate integrally regarding the rotating direction.

In this second embodiment, a mechanism in which the chucking conveyer mechanism 130 receives the cylindrical container B from the spiral chute mechanism 50, chucks and conveys it and delivers it to the subsequent spiral chute mechanism 60 is similar to the mechanism in the first embodiment except that the vacuum suction device 31 in the first embodiment is replaced by the chucking device 131 (See FIG. 9).

Here, an operation of sterilizing the cylindrical container B by using the continuous sterilization system 200 according to the second embodiment configured as above and of carrying this sterilized cylindrical container B into the aseptic workroom will be described.

In FIG. 1, the continuous sterilization system 200 and the aseptic workroom (not shown) installed consecutively to the side surface on the right side in the figure of this continuous sterilization system 200 are both under the aseptic environment, and a filling work of pharmaceutical products is performed inside the aseptic workroom. At this time, the shutters 11a and 12a of the carrying-in port 11 and the carrying-out port 12 of the continuous sterilization system 200 are opened, the cylindrical containers B before sterilization are continuously carried into the continuous sterilization system 200, and the cylindrical containers B sterilized in the continuous sterilization system 200 are continuously carried into the aseptic workroom.

This second embodiment has, as described above, a structure similar to the first embodiment except that the adsorption conveyer mechanism 30 is changed to the chucking conveyer mechanism 130, and a sterilization target to be sterilized by the continuous sterilization system is also the cylindrical container B having the structure similar to that of the first embodiment. Therefore, since the explanation other than the structure of the chucking conveyer mechanism 130 and its operation is overlapped with the explanation in the first embodiment, it will be omitted.

Thus, here, a state after the cylindrical container B is conveyed on the belt conveyer 51 of the spiral chute mechanism 50 and has reached the end portion in the traveling direction of the belt conveyer 51 will be described (See FIG. 12). Below the end portion in the traveling direction of the belt conveyer 51, the chucking conveyer mechanism 130 is arranged, and the belt conveyer 51 and the chucking conveyer mechanism 130 are connected by the two parallel guides 52 of the spiral chute mechanism 50.

Figure 12:
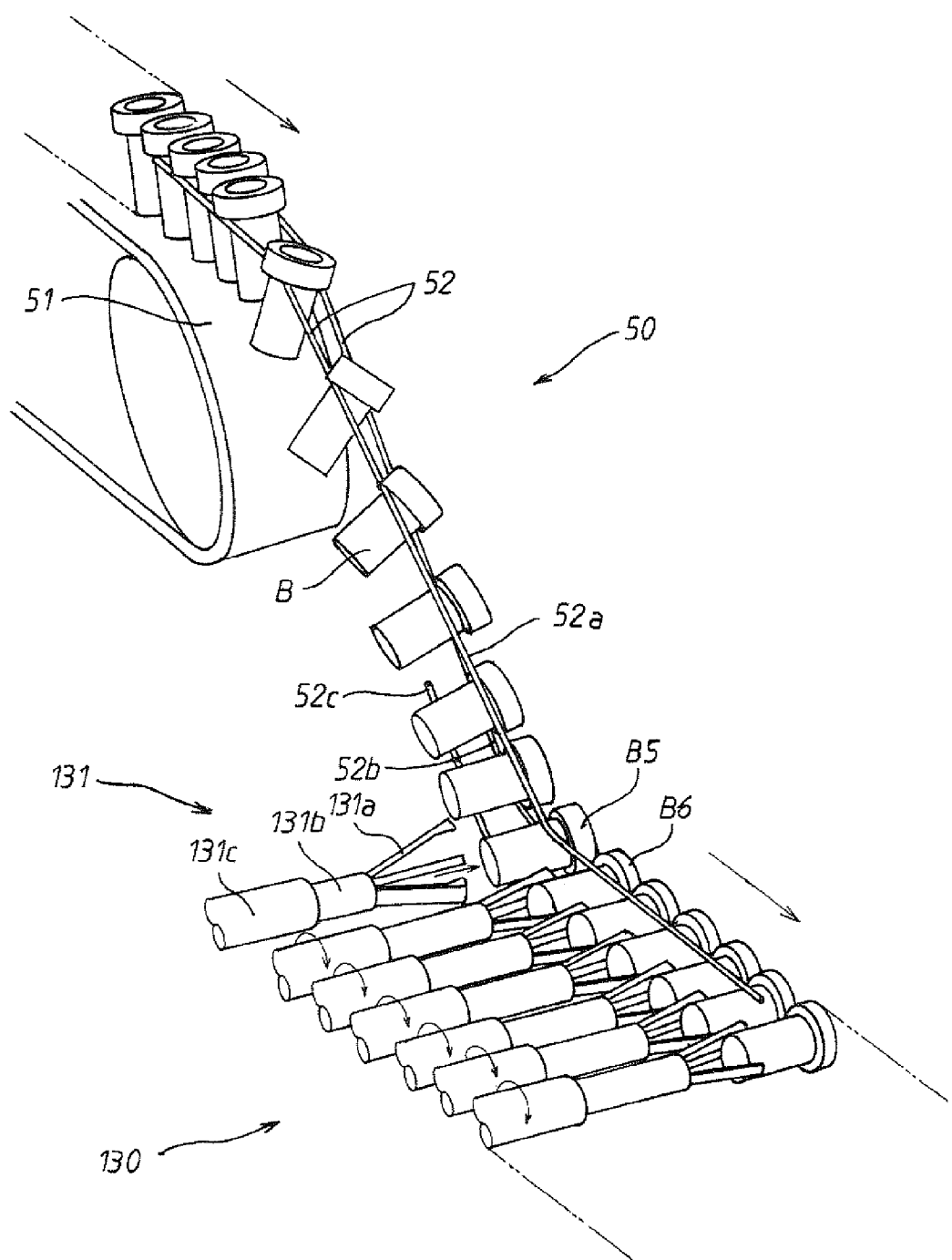
FIG. 12 is a perspective view illustrating a state in which the cylindrical container is reversed by a first spiral chute mechanism in the continuous sterilization system according to the second embodiment.

The cylindrical containers B having been conveyed by the belt conveyer 51 in a single row in the upright state are, as illustrated in FIG. 12, supported by the two parallel guides 52 arranged in the horizontal positional relationship on the end portion in the traveling direction of the belt conveyer 51 on the body portion Bb and the neck portion Bc from the both sides and in the upright state. At this time, the outer surfaces of the bottom portion Bd of the cylindrical container B and the lower portion Be of the body portion in the vicinity thereof are kept in the state sterilized by the previous electron beam irradiation by the electron beam accelerator E1.

Subsequently, the cylindrical container B separates away from the end portion in the traveling direction of the belt conveyer 51 and spirally drops while being gradually inclined downward and assisted by the two parallel guides 52. At this time, the cylindrical container B is reversed from the upright state by approximately 90 degrees to the laterally directed state and moves to the height of the chucking conveyer mechanism 130.

In this state, the cylindrical container B is, as illustrated in FIG. 12, supported on the body portion Bb and the neck portion Bc from the both sides by the two parallel guides (52a, 52b) arranged in the perpendicular positional relationship with each other in the laterally directed state after being reversed by approximately 90 degrees from the upright state. Moreover, the cylindrical container B is supported more stably in the laterally directed state by the auxiliary guide 52c arranged in the horizontal positional relationship with the one parallel guide 52b.

Subsequently, the cylindrical container B having reached the chucking conveyer mechanism 130 (a state of B5 in FIG. 12) is supported by the chucking device 131 by its lower portion Be of the body portion thereof (a state of B6 in FIG. 12). That is, as described above, the inner cylindrical tube 131b of the chucking device 131 is pulled out to the outside of the outer cylindrical tube 131c and extends and approaches the cylindrical container B from its bottom portion Bd side, and the three claws 131a close and support the lower portion Be of the body portion of the cylindrical container B.

The three claws 131a of the chucking device 131 have been fully sterilized in advance, and even if the lower portion Be of the body portion of the cylindrical container B sterilized by the electron beam irradiation from the electron beam accelerator E1 is chucked by the three claws 131a, the lower portion Be of the body portion is not contaminated again.

As described above, the cylindrical container B supported by being chucked by the chucking device 131 on its lower portion Be of the body portion rotates together with the inner cylindrical tube 131b and the outer cylindrical tube 131c around their tube shafts by driving of the rotary motor 132 as described above. Moreover, this cylindrical container B circularly moves in the conveying direction by driving of the circularly moving conveyer 133 as described above.

Subsequently, the cylindrical container B supported by the chucking device 131 is conveyed to the upper position of the irradiation port E2a of the electron beam accelerator E2 while rotating together with the inner cylindrical tube 131b and the outer cylindrical tube 131c around their tube shafts (See FIG. 13). Here, the outer surfaces of the body portion Bb of the cylindrical container B being conveyed (a portion not chucked by the three claws 131a) and the neck portion Bc are sterilized by the electron beam emitted from the irradiation port E2a of the electron beam accelerator E2.

Here, since the cylindrical container B rotates together with the chucking device 131 around its tube shaft, this cylindrical container B is sterilized over the entire periphery of its side surface. At this time, by controlling the rotating speed and circularly moving speed of the chucking device 131, the opening diameter of the irradiation port E2a, and the electron beam strength, the outer surfaces of the body portion Bb and the neck portion Bc of the cylindrical container B are fully sterilized.

Subsequently, the cylindrical container B supported by the chucking device 131 is conveyed to the front position of the irradiation port E3a of the electron beam accelerator E3 (See FIG. 14). Here, the upper surface Bf of the neck portion Bc of the cylindrical container B being conveyed and an inner surface of the accommodating portion Ba are sterilized by the electron beam emitted from the irradiation port E3a of the electron beam accelerator E3. At this time, by controlling the circularly moving speed of the chucking device 131, the opening diameter of the irradiation port E3a, and the electron beam strength, the upper surface Bf of the neck portion Bc of the cylindrical container B and the inner surface of the accommodating portion Ba are fully sterilized.

As described above, in the cylindrical container B, the entire inner and outer surfaces of the bottom portion Bd, the body portion Bb, and the neck portion Bc as well as the upper surface Bf of the neck portion Bc and the accommodating portion Ba are fully sterilized.

Figure 15:
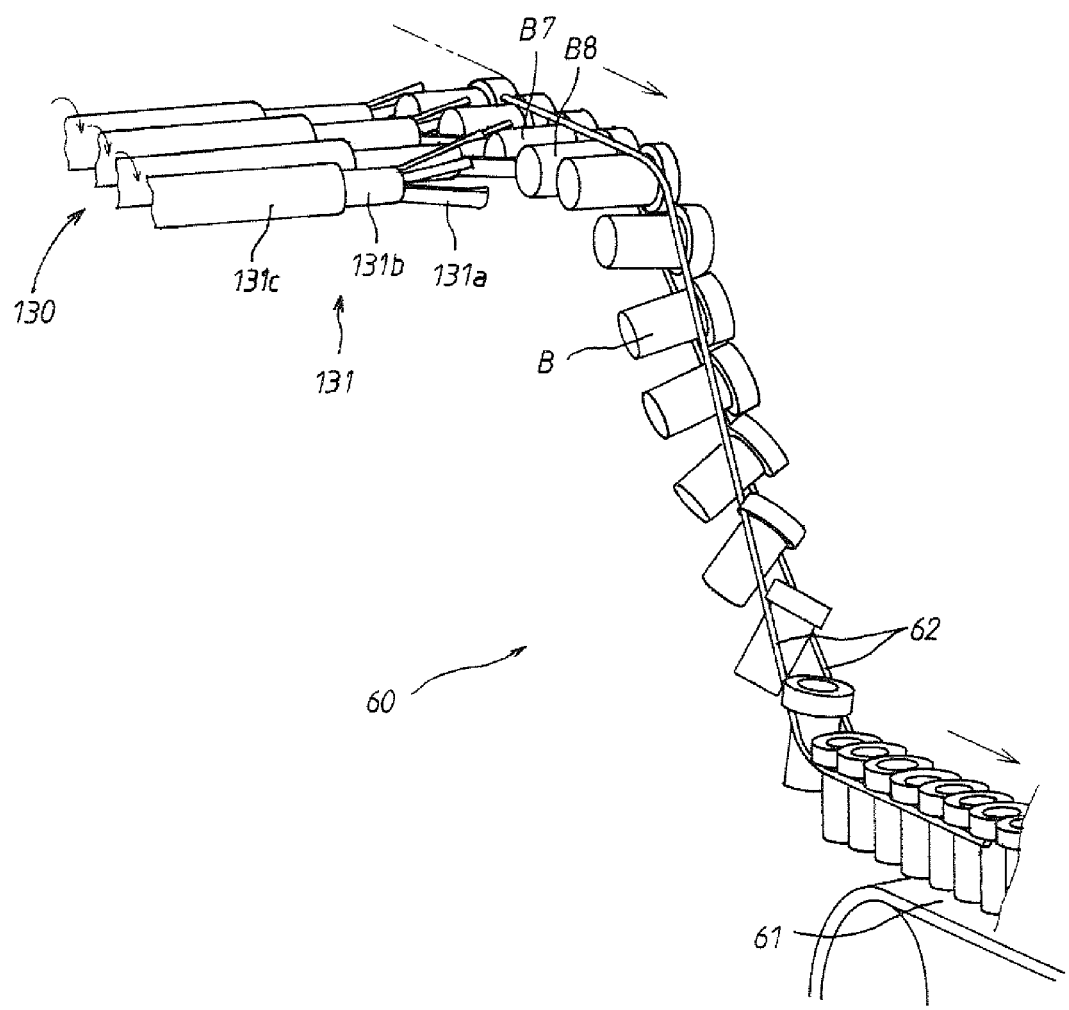
FIG. 15 is a perspective view illustrating a state in which the cylindrical container is reversed by a second spiral chute mechanism in the continuous sterilization system according to the second embodiment.

Subsequently the cylindrical container B having been fully sterilized on the entire inner and outer surfaces and having reached the end portion in the traveling direction of the chucking conveyer mechanism 130 is supported by the chucking device 131 on its lower portion Be of the body portion (state of B7 in FIG. 15). Here, the chucking device 131 releases the bottom portion Bd of the cylindrical container B from chucking and also separates away from the bottom portion Bd side (state of B8 in FIG. 15). At this time, the cylindrical container B is supported on the body portion Bb and the neck portion Bc from the both sides by the two parallel guides 62 arranged in the perpendicular positional relationship with each other still in the laterally directed state.

The two parallel guides 62 have been fully sterilized in advance, and even if the body portion Bb and the neck portion Bc of the cylindrical container B whose entire inner and outer surfaces have been sterilized by the electron beam irradiation of the electron beam accelerators E1 to E3 are in contact with them, the portions are not contaminated again.

Subsequently, the cylindrical container B is reversed from the laterally directed state by approximately 90 degrees to the upright state and moved to the height of the belt conveyer 61 while being assisted by the two parallel guides 62 and gradually dropping downward spirally. In this state, the cylindrical containers B are, as illustrated in FIG. 15, reversed from the laterally directed state by approximately 90 degrees to the upright state and supported on the body portion Bb and the neck portion Bc from the both sides by the two parallel guides 62 arranged in the horizontal positional relationship and are aligned in a single row in the traveling direction of the belt conveyer 61.

The belt of the belt conveyer 61 has been fully sterilized in advance, and even if the bottom portion Bd of the cylindrical container B whose entire inner and outer surfaces have been sterilized by electron beam irradiation of the electron beam accelerators E1 to E3 is brought into contact, this bottom portion Bd is not contaminated again.

Subsequently, the cylindrical containers B are conveyed by the belt conveyer 61 to the position of the belt conveyer mechanism 70 similarly to the first embodiment, and after that, aligned in a single row still in the upright state and conveyed to the carrying-out port 12 while changing its traveling direction by the plurality of belt conveyers and guides (none of them is illustrated) of the belt conveyer mechanism 70 and carried into the aseptic workroom through the shutter 12a (See FIGS. 1 and 2).

Third Embodiment

Subsequently, a third embodiment of a continuous sterilization system according to the present invention will be described in accordance with the attached drawings. In the continuous sterilization system 300 according to the third embodiment, the position of the star-wheel conveyer mechanism 20 and the position of the adsorption conveyer mechanism 30 in the first embodiment are exchanged with each other. Moreover, the spiral chute mechanism 50 in the first embodiment is changed to a screw-conveyer mechanism 80, while the other portions have a structure similar to that of the first embodiment (See FIGS. 16, 17, and 18). Moreover, a sterilization target to be sterilized by the continuous sterilization system according to this third embodiment is also the cylindrical container B having the structure similar to that of the first embodiment (See FIG. 3).

That is, inside the chamber 10, the star-wheel conveyer mechanism 20 and the adsorption conveyer mechanism 30 for supporting and conveying the cylindrical container B in order to emit the electron beam as well as the three electron beam accelerators E1, E2, and E3 for irradiating the electron beam to each portion of the cylindrical container B being conveyed by them for sterilization are provided.

Moreover, inside the chamber 10, the belt conveyer mechanism 40 for conveying the cylindrical container B from the carrying-in port 11, the screw-conveyer mechanism 80 for delivery from the belt conveyer mechanism 40 to the adsorption conveyer mechanism 30, the spiral chute mechanism 60 for delivery from the adsorption conveyer mechanism 30 to the star-wheel conveyer mechanism 20, and the belt conveyer mechanism 70 for receiving the cylindrical container B from the star-wheel conveyer mechanism 20 and conveying it to the carrying-out port 12 are provided.

In this third embodiment, the adsorption conveyer mechanism 30 is located at the center part of the chamber 10 similarly to the adsorption conveyer mechanism 30 in the first embodiment (See FIGS. 16 and 17) and has a plurality of vacuum suction devices 31, the circularly moving conveyer 33 for circularly moving the vacuum suction device 31, and the rotary motor 32 for driving the circularly moving conveyer 33 and rotating this vacuum suction device 31. Here, the configuration and working mechanism of each portion in the adsorption conveyer mechanism 30 are the same as those in the first embodiment. Moreover, in this third embodiment, the electron beam accelerators E2 and E3 are provided on conveying portions by the adsorption conveyer mechanism 30 similarly to the first embodiment.

Figure 16:
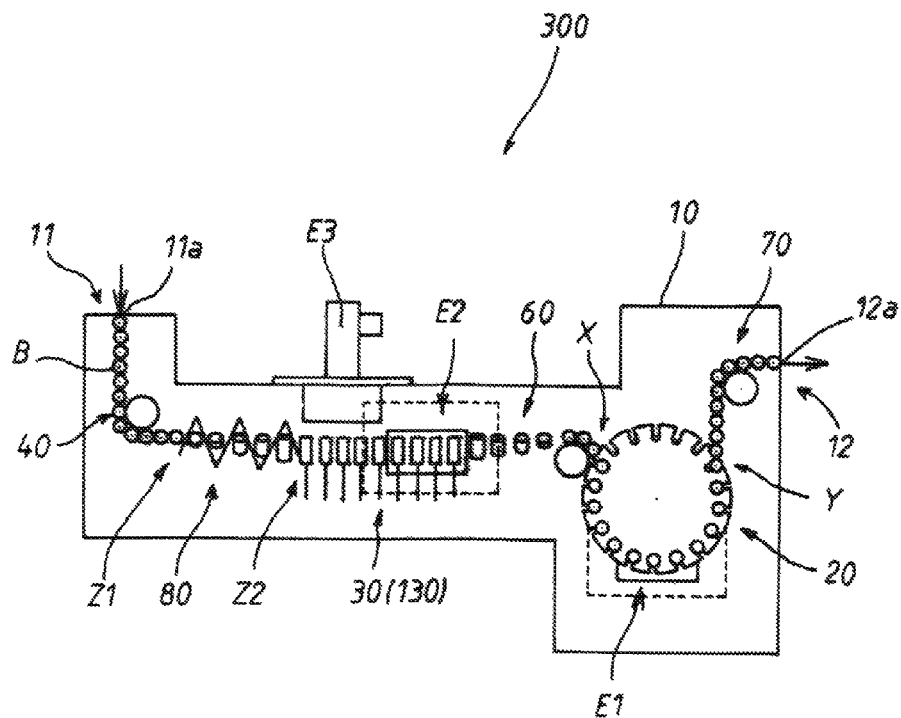
FIG. 16 is a plan view illustrating an outline of a continuous sterilization system according to a third embodiment.
Figure 17:
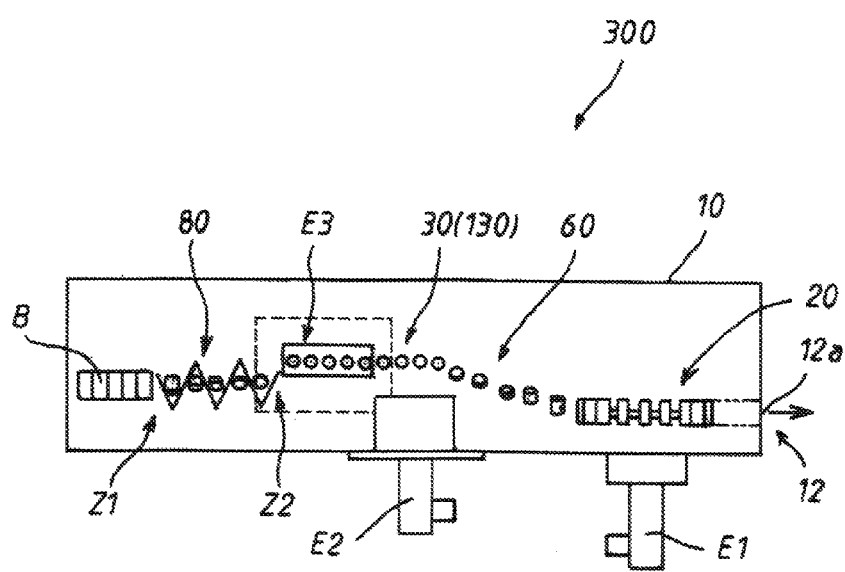
FIG. 17 is a front view illustrating an outline of the continuous sterilization system according to the third embodiment.

In this third embodiment, the star-wheel conveyer mechanism 20 is, as illustrated in FIGS. 16 and 17, located on the right-side portion of the chamber 10 (on the carrying-out port 12 side) and has the star wheel 21 and the rotary motor 22 for rotating this star wheel 21 around a center axis of its disk face 21a. Here, the configuration and working mechanism of each portion in the star-wheel conveyer mechanism 20 are the same as those in the first embodiment. Moreover, in this third embodiment, the electron beam accelerator E1 is provided on a conveying portion by the star-wheel conveyer mechanism 20 similarly to the first embodiment.

Figure 18:
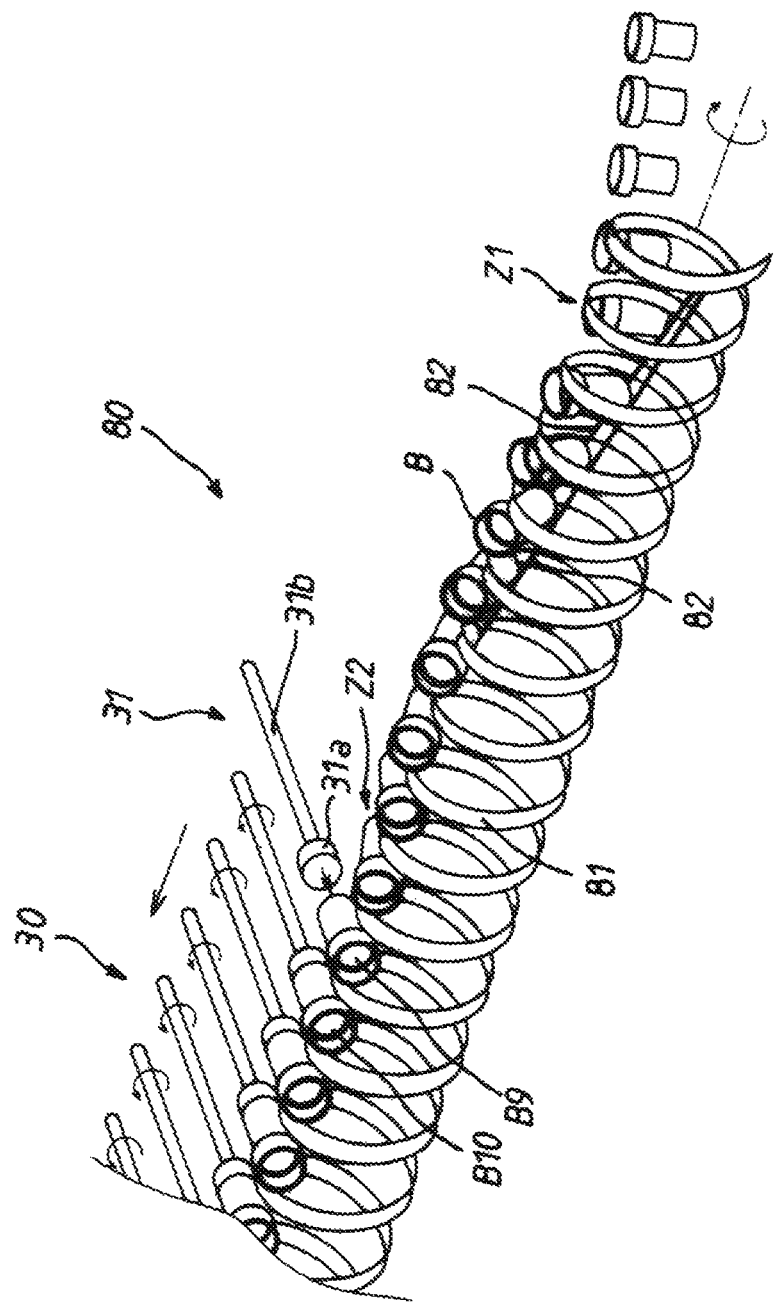
FIG. 18 is a perspective view illustrating a state in which the cylindrical container is reversed by a screw-conveyer mechanism in the continuous sterilization system according to the third embodiment.

The screw-conveyer mechanism 80 has, as illustrated in FIG. 18, a screw conveyer 81 and two guides 82. The screw conveyer 81 forms a spiral in the horizontal direction and rotates while supporting the side surface of the cylindrical container B in a groove portion of this spiral. The two guides 82 are disposed to the position of the adsorption conveyer mechanism 30 so as to support the bottom surface of the cylindrical container B and to reverse the cylindrical container B by approximately 90 degrees from the upright state to the laterally directed state with rotation of the screw conveyer 81.

Here, an operation of sterilizing the cylindrical container B using the continuous sterilization system 300 according to this third embodiment configured as above and of carrying this sterilized cylindrical container B into the aseptic workroom will be described.

In FIG. 16, the continuous sterilization system 300 and the aseptic workroom (not shown) installed consecutively to the side surface on the right side in the figure of this continuous sterilization system 300 are both under the aseptic environment, and a filling work of pharmaceutical products is performed inside the aseptic workroom. At this time, the shutters 11a and 12a of the carrying-in port 11 and the carrying-out port 12 of the continuous sterilization system 300 are opened, the cylindrical containers B before sterilization are continuously carried into the continuous sterilization system 300, and the cylindrical containers B sterilized in the continuous sterilization system 300 are continuously carried into the aseptic workroom.

In such a state, the cylindrical container B carried into the continuous sterilization system 300 from the outside environment is first conveyed by the belt conveyer 41 of the belt conveyer mechanism 40 to a receiving position Z1 of the screw-conveyer mechanism 80 (See FIG. 16) aligned in a single row in the upright state.

Subsequently, the cylindrical container B is, as illustrated in FIG. 18, supported in the upright state by the screw conveyer 81 rotating counterclockwise in the figure (Z1 position in FIG. 18). Specifically, the cylindrical container B is supported one by one in a groove portion between peaks of the spiral of the screw conveyer 81 on its body portion Bb. At this time, the bottom portion Bd of the cylindrical container B is supported by two guides 82.

As described above, the cylindrical containers B supported at equal intervals in the groove portions of the spiral of the screw conveyer 81 are conveyed to an end portion Z2 of the adsorption conveyer mechanism 30 with clockwise rotation in the figure of the screw conveyer 81 while being guided by the two guides 82 and reversing its direction by approximately 90 degrees from the upright state to the laterally directed state.

In this state, the cylindrical container B has been reversed by approximately 90 degrees from the upright state to the laterally directed state, as illustrated in FIG. 18, and stably supported by the groove portions of the screw conveyer 81 and the two guides 82 on the body portion Bb and the bottom portion Bd.

Subsequently, the cylindrical container B having reached the end portion Z2 of the adsorption conveyer mechanism 30 (a state of B9 in FIG. 18) is supported by the vacuum suction device 31 on its bottom portion Bd (a state of B10 in FIG. 18). That is, as described above, the vacuum suction device 31 approaches the cylindrical container B from its bottom portion Bd side, brings the vacuum suction port 31a into contact with the bottom portion Bd and supports it by vacuum-suctioning. A suctioning force of this vacuum suction port 31a is, as described above, realized by a vacuum pump (not shown) connected through the suction tube 31b.

As described above, the cylindrical container B vacuum-suctioned by the vacuum suction device 31 on its bottom portion Bd and supported is rotated by driving of the rotary motor 32 together with the vacuum suction port 31a and the suction tube 31b around their cylindrical shafts. Moreover, this cylindrical container B is circularly moved by driving of the circularly moving conveyer 33 in the conveying direction as described above.

Subsequently, the cylindrical container B supported by the vacuum suction device 31 is conveyed to the front position of the irradiation port E3a of the electron beam accelerator E3 while rotating together with the vacuum suction port 31a and the suction tube 31b around their cylindrical shafts (similar to FIG. 7 in the first embodiment). Here, the upper surface Bf of the neck portion Bc and the inner surface of the accommodating portion Ba of the cylindrical container B being conveyed are sterilized by the electron beam emitted from the irradiation port E3a of the electron beam accelerator E3. At this time, by controlling the circularly moving speed of the vacuum suction device 31, the opening diameter of the irradiation port E3a, and the electron beam strength, the upper surface Bf of the neck portion Bc and an inner surface of the accommodating portion Ba of the cylindrical container B are fully sterilized.

Subsequently, the cylindrical container B supported by the vacuum suction device 31 is conveyed to the upper position of the irradiation port E2a of the electron beam accelerator E2 while rotating together with the vacuum suction port 31a and the suction tube 31b around these cylindrical shafts (similar to FIG. 6 in the first embodiment). Here, the outer surfaces of the body portion Bb and the neck portion Bc of the cylindrical container B being conveyed are sterilized by the electron beam emitted from the irradiation port E2a of the electron beam accelerator E2.

Here, since the cylindrical container B is rotating together with the vacuum suction device 31 around its cylindrical shaft, this cylindrical container B is sterilized over the entire periphery of its side surface. At this time, by controlling the rotating speed and circularly moving speed of the vacuum suction device 31, the opening diameter of the irradiation port E2a, and the electron beam strength, the outer surfaces of the body portion Bb and the neck portion Bc of the cylindrical container B are fully sterilized.

As described above, in the cylindrical container B, excluding its bottom portion Bd, the body portion Bb, and the neck portion Bc as well as the upper surface Bf and the entire inner and outer surfaces of the accommodating portion Ba of the cylindrical container B are fully sterilized.

Subsequently the cylindrical container B having been sterilized on the entire inner and outer surfaces excluding the bottom portion Bd and having reached the end portion in the traveling direction of the adsorption conveyer mechanism 30 is supported by the vacuum suction device 31 on its bottom portion Bd (similar to the state of B3 in FIG. 10 in the first embodiment). Here, as described above, the vacuum suction device 31 releases the bottom portion Bd of the cylindrical container B from vacuum suctioning and also separates away from the bottom portion Bd side (state of B4 in FIG. 10). At this time, the cylindrical container B is supported on the body portion Bb and the neck portion Bc from the both sides by the two parallel guides 62 arranged in the perpendicular positional relationship with each other still in the laterally directed state.

The two parallel guides 62 have been fully sterilized in advance, and even if the body portion Bb and the neck portion Bc of the cylindrical container B whose entire inner and outer surfaces except the bottom portion Bd have been sterilized by the electron beam irradiation of the electron beam accelerators E2 and E3 are in contact with them, the portions are not contaminated again.

Subsequently, the cylindrical container B is reversed from the laterally directed state by approximately 90 degrees to the upright state and moved to the height of the belt conveyer 61 while being assisted by the two parallel guides 62 and gradually dropping downward spirally. In this state, the cylindrical container B is, as illustrated in FIG. 10, reversed from the laterally directed state by approximately 90 degrees to the upright state and supported on the body portion Bb and the neck portion Bc from the both sides by the two parallel guides 62 arranged in the horizontal positional relationship and are aligned in a single row in the traveling direction of the belt conveyer 61.

Subsequently, the cylindrical containers B are conveyed to the receiving position X of the star wheel 21 of the star-wheel conveyer mechanism 20 in the state aligned in a single row and in the upright state (See FIG. 16).

Subsequently, the cylindrical containers B are, as illustrated in FIG. 4, supported in the upright state by the star wheel 21 rotating counterclockwise in the figure through the rotating shaft 21d (X position in FIG. 4). Specifically, the cylindrical containers B are supported one by one by the recess portion 21c provided at equal intervals on the outer edge portion 21b of the star wheel 21 on its body portion Bb and the neck portion Bc. At this time, outer surfaces of the bottom portion Bd of the cylindrical container B and the lower portion Be of the body portion in the vicinity thereof are not in contact with the recess portion 21c of the star wheel 21.

The star wheel 21 of the star-wheel conveyer mechanism 20 has been fully sterilized in advance, and even if the body portion Bb and the neck portion Bc of the cylindrical container B sterilized by the electron beam irradiation from the electron beam accelerators E2 and E3 are supported by the star wheel 21, the body portion Bb and the neck portion Bc are not contaminated again.

As described above, the cylindrical containers B supported by the outer edge portion 21b of the star wheel 21 at equal intervals are conveyed to the upper position of the irradiation port E1a of the electron beam accelerator E1 counterclockwise in the figure along the outer edge portion 21b of the star wheel 21 (See FIG. 4). Here, the outer surfaces of the bottom portion Bd of the cylindrical container B being conveyed and the lower portion Be of the body portion in the vicinity thereof are sterilized by the electron beam emitted from the irradiation port E1a of the electron beam accelerator E1. At this time, by controlling the rotating speed of the star wheel 21, the opening diameter of the irradiation port E1a, and the electron beam strength, the outer surfaces of the bottom portion Bd of the cylindrical container B and the lower portion Be of the body portion in the vicinity thereof are fully sterilized.

As described above, in the cylindrical container B, its bottom portion Bd, the body portion Bb, and the neck portion Bc as well as the upper surface Bf of the neck portion Bc and the entire inner and outer surfaces of the accommodating portion Ba are fully sterilized.

Subsequently, the cylindrical container B whose entire inner and outer surfaces have been fully sterilized is further conveyed counterclockwise in the figure along the outer edge portion 21b of the star wheel 21 and conveyed to the delivery position Y. At this delivery position Y, the belt conveyer of the belt conveyer mechanism 70 (not shown in FIG. 4) is arranged, and the cylindrical containers B having been conveyed to the delivery position Y are guided by a guide (not shown), received in the upright state on the belt conveyer, and aligned in a single row in the traveling direction of the belt conveyer.

The belt of the belt conveyer has been fully sterilized in advance, and even if the bottom portion Bd of the cylindrical container B having been sterilized by electron beam irradiation from the electron beam accelerator E1 is brought into contact, this bottom portion Bd is not contaminated again.

Subsequently, the cylindrical container B is conveyed by the belt conveyer and the guide (none of them is shown) to the carrying-out port 12, still in the upright state and aligned in a single row, though not particularly illustrated, and carried into the aseptic workroom through the shutter 12a (See FIGS. 16 and 17).

As described above, in the continuous sterilization system according to each of the above described embodiments, since the low-energy type electron beam accelerator is employed, a heavy and thick X-ray protective wall is not required, but the system can be incorporated inline in the aseptic workroom. As a result, a manufacturing cost of the system itself is low, and maintenance is facilitated. Moreover, since the low-energy type electron beam accelerator is employed, sterilization processing can be executed at a low temperature, and even if the cylindrical container is made of plastic, the container is not damaged. Furthermore, no residues remain in the sterilized cylindrical container, and safe and easy-to-handle sterilizing means can be provided.

Moreover, in the continuous sterilization system according to each of the embodiments, since the electron beam is emitted while the portion for supporting the cylindrical container is changed, uniform irradiation periods can be ensured stably on any portion of the inner and outer surfaces. During such series of operations, the cylindrical container has its entire inner and outer surfaces reliably sterilized, and a portion sterilized by the electron beam irradiation is not contaminated again.

Moreover, the cylindrical container is conveyed in the continuous sterilization system by being supported on some portion all the time. That is, in the star-wheel conveyer mechanism, the recess portion of the star wheel supports the body portion and the neck portion of the cylindrical container, while in the adsorption conveyer mechanism, the vacuum suction device supports the bottom portion of the cylindrical container. Moreover, in the chucking conveyer mechanism, the chucking device supports the lower portion of the body portion of the cylindrical container. As described above, since the cylindrical container is applied with irradiation of the electron beam in the reliably supported state, the cylindrical container is not tipped over or dislocated and the sterilization becomes ununiform during the sterilization process.

Moreover, by means of uniform rotation of the star wheel, uniform rotation and stable circular movement of the vacuum suction device or the chucking device, and setting of the irradiation condition of each of the electron beam accelerators, the cylindrical container has its entire inner and outer surfaces reliably sterilized, and a portion sterilized by the electron beam irradiation is not contaminated again.

Thus, in each of the above described embodiments, the continuous sterilization system can be provided in which the sterilization target is reliably supported and is not tipped over during the sterilization process, uniform irradiation periods can be ensured stably for any portion on the inner and outer surfaces, and a portion sterilized by the electron beam irradiation is not contaminated again.

In practice of the present invention, not limited to the above embodiments, the following various variations can be cited:

(1) In each of the above described embodiments, the bottom portion of the cylindrical container and the body portion in the vicinity thereof are sterilized during conveyance by the star-wheel conveyer mechanism, and the body portion and the neck portion of the cylindrical container and the accommodating portion are sterilized during conveyance by the adsorption conveyer mechanism or the chucking conveyer mechanism, but this is not limiting, and the accommodating portion and the like in addition to the bottom portion and the like may be sterilized during conveyance by the star-wheel conveyer mechanism.

(2) In each of the above described embodiments, the cylindrical container is conveyed by frequently using the combination of the belt conveyer and the two parallel guides, but this is not limiting, and other conveying methods such as another conveyer mechanism or a lift mechanism may be employed. In this case, any mechanism can be used as long as the electron beam can be emitted to a portion other than the portion supporting the cylindrical container, and all the inner and outer surfaces can be sterilized while this supporting position is changed.

(3) In each of the above described embodiments, the cylindrical container is a sterilization target, but this is not limiting, and a cylindrical container having a triangular prism or a quadrangular prism shape or a cylindrical container having a complicated shape such as a bottle may be employed. If these cylindrical containers can be stably sterilized by the continuous sterilization system in each of the above described embodiments, they can be targets of the present invention.

(4) The cylindrical container in each of the above described embodiments has the neck portion projecting to the side surface more largely than the body portion, and the two parallel guides of each conveying means perform conveyance by supporting the body portion and the neck portion. Particularly, in each of the spiral chute mechanisms, the cylindrical container drops downward and is reversed while being supported by the two parallel guides on the body portion and the neck portion. However, the shape of the cylindrical container is not limited to that, and the projecting portion to the side surface may be provided at two spots or more. Moreover, not a projecting portion but a recess portion may be provided on the side surface. In either case, it is only necessary to consider the shape of the cylindrical container and the number and arrangement of the guides so that the cylindrical container can be conveyed and reversed easily and stably.

(5) In the first and second embodiments, the cylindrical container is reversed by the two spiral chute mechanisms from the upright state to the laterally directed state and reversed again from the laterally directed state to the upright state and sterilized. However, without reversing twice as above, sterilization may be performed while the cylindrical container stays in the upright state throughout all the processes and is conveyed by the star-wheel conveyer mechanism and the adsorption conveyer mechanism or the chucking conveyer mechanism. Alternatively, sterilization may be performed while the cylindrical container stays in the laterally directed state throughout all the processes and is conveyed by the star-wheel conveyer mechanism and the adsorption conveyer mechanism or the chucking conveyer mechanism.

(6) In the above described first and second embodiments, the cylindrical container is reversed by the two spiral chute mechanisms. On the other hand, in the third embodiment, the cylindrical container is reversed by the one screw-conveyer mechanism and the one spiral chute mechanism. As described above, as a reversing mechanism for the cylindrical container, the spiral chute mechanism, the screw-conveyer mechanism and other reversing mechanisms may be used singularly or in a combination.

(7) In each of the above described embodiments, the star-wheel conveyer mechanism, the adsorption conveyer mechanism, and the chucking conveyer mechanism are provided with driving mechanisms, respectively, and their driving might cause dusts in the chamber. Such dusts prevent manufacture of pharmaceutical products as contaminants other than microorganisms as sterilization targets. Thus, in the continuous sterilization system in each of the above described embodiments, a suction station is preferably provided in the vicinity of each of the driving portions so that the dusts generated from the driving portion is suctioned and the inside of the chamber is cleaned.

(8) In the second embodiment, the three-claw type is employed for the chucking device of the chucking conveyer mechanism, but the three-claw type is not limiting, and any type may be employed such as a two-claw type or a four-claw type or more as long as the cylindrical container can be stably supported and rotated.

(9) In the second embodiment, the three claws of the chucking device of the chucking conveyer mechanism support the outer side surface of the cylindrical container from the outside, but this is not limiting, and any position may be supported depending on the shape of the container to be supported. For example, a recess portion may be formed on the bottom portion of the cylindrical container so that an inner side surface of this recess portion is supported from the inside.

(10) In each of the above described embodiments, a chain conveyer mechanism using a sprocket and a chain belt as a circularly moving conveyer is employed, and each of the vacuum suction devices is circularly moved, but this is not limiting, and each of the vacuum suction devices may be circularly moved by the screw-conveyer mechanism or the belt conveyer mechanism.

REFERENCE SIGNS LIST 100, 200, 300 continuous sterilization system
10 chamber
11 carrying-in port
12 carrying-out port
11a, 12a shutter
20 star-wheel conveyer mechanism
21 star wheel
21a disk face
21b outer edge portion
21c recess portion
21d rotating shaft
22 rotary motor
30 adsorption conveyer mechanism
31 vacuum suction device
31a vacuum suction port
31b suction tube
31c pinion gear 32 rotary motor
33 circularly moving conveyer
34 sprocket
35 chain belt
36 slide guide
37 rack gear
40, 70 belt conveyer mechanism
50, 60 spiral chute mechanism
41, 51, 61 belt conveyer
42, 52, 62 parallel guide
80 screw-conveyer mechanism
81 screw conveyer
82 guide
130 chucking conveyer mechanism
131 chucking device
131a claw
131b inner cylindrical tube
131c outer cylindrical tube
132 rotary motor
133 circularly moving conveyer
B cylindrical container
Ba accommodating portion
Bb body portion
Bc neck portion
Bd bottom portion
E1, E2, E3 electron beam accelerator
E1a, E2a, E3a irradiation port

The invention claimed is:

1. A continuous sterilization system comprising:
first conveying means for continuously conveying a cylindrical container by supporting the same from a side surface;
a first electron beam accelerator for emitting an electron beam from the bottom surface portion side of said cylindrical container during conveyance by this first conveying means;
second conveying means for continuously conveying said cylindrical container by supporting the same from the bottom surface portion side having been sterilized by electron beam irradiation by said first electron beam accelerator while rotating the same along a cylindrical shaft core of the cylindrical container;
a second electron beam accelerator for emitting the electron beam over the entire periphery from the side surface portion side of said cylindrical container during conveyance by this second conveying means; and
a third electron beam accelerator for emitting the electron beam from the opening portion side to an inner surface portion of said cylindrical container during conveyance by said first conveying means or said second conveying means.

2. The continuous sterilization system according to claim 1, wherein
said first conveying means has a star wheel on which a plurality of support portions, each supporting said cylindrical container from its side surface, are provided on an outer periphery; and
a first rotating member for rotating this star wheel around its center axis.

3. A continuous sterilization system comprising:
second conveying means for continuously conveying a cylindrical container by supporting the same from a bottom surface portion side while rotating the same along a cylindrical shaft core of the cylindrical container;
a second electron beam accelerator for emitting an electron beam over the entire periphery from the side surface portion side of said cylindrical container over the entire periphery during conveyance by this second conveying means;
first conveying means for continuously conveying said cylindrical container by supporting the same from the side surface having been sterilized by electron beam irradiation by said second electron beam accelerator;
a first electron beam accelerator for emitting the electron beam from the bottom surface portion side of said cylindrical container during conveyance by this first conveying means; and
a third electron beam accelerator for emitting the electron beam from the opening portion side to an inner surface portion of said cylindrical container during conveyance by said second conveying means or said first conveying means.

4. The continuous sterilization system according to claim 3, wherein
said first conveying means has a star wheel on which a plurality of support portions, each supporting said cylindrical container from its side surface, are provided on an outer periphery; and
a first rotating member for rotating this star wheel around its center axis.

5. The continuous sterilization system according to any one of claim 1 to 2 or 4, characterized in that
said second conveying means has a suction member for supporting said cylindrical container by vacuum-suctioning the same from the bottom surface;
a second rotating member for rotating this suction member together with said cylindrical container supported by the suction member along a cylindrical shaft core of the cylindrical container; and
a first transfer member for transferring said suction member together with said cylindrical container supported by the suction member in a direction intersecting the cylindrical shaft core of the cylindrical container.

6. The continuous sterilization system according to any one of claim 1 to 2 or 4, characterized in that
said second conveying means has a chucking member for supporting said cylindrical container from the bottom surface portion side by chucking;
a third rotating member for rotating this chucking member together with said cylindrical container supported by the chucking member along the cylindrical shaft core of the cylindrical container; and
a second transfer member for transferring said chucking member together with said cylindrical container supported by the chucking member in a direction intersecting the cylindrical shaft core of the cylindrical container.

7. A continuous sterilization system comprising:
a chamber having a carrying-in port for carrying in the cylindrical container and a carrying-out port for carrying out the same;
supply means for supplying a plurality of the cylindrical containers carried into said chamber through said carrying-in port;
first conveying means having a star wheel on which a plurality of support portions, each supporting said cylindrical container supplied by this supply means from its side surface, are provided on an outer periphery and a first rotating member for rotating this star wheel around its center axis and continuously conveying said cylindrical container;

a first electron beam accelerator for emitting an electron beam from the bottom surface portion side of said cylindrical container during conveyance by this first conveying means;

first reversing means for receiving said cylindrical container from said first conveying means and reversing its cylindrical shaft core by approximately 90 degrees;

second conveying means having a suction member for receiving said cylindrical container from this first reversing means and supporting the cylindrical container from a bottom surface by vacuum-suctioning, a second rotating member for rotating this suction member together with said cylindrical container supported by the suction member along the cylindrical shaft core of the cylindrical container, and a first transfer member for transferring said suction member together with said cylindrical container supported by the suction member in a direction intersecting the cylindrical shaft core of the cylindrical container and continuously conveying said cylindrical container;

a second electron beam accelerator for emitting the electron beam over the entire periphery from the side surface portion side of said cylindrical container during conveyance by this second conveying means;

a third electron beam accelerator for emitting the electron beam from the opening portion side to the inner surface portion of said cylindrical container during conveyance by said second conveying means;

second reversing means for receiving said cylindrical container from said second conveying means and reversing its cylindrical shaft core by approximately 90 degrees again; and carrying-out means for receiving said cylindrical container from this second reversing means and carrying out the cylindrical container to the outside of said chamber through said carrying-out port.

8. A continuous sterilization system comprising:

a chamber having a carrying-in port for carrying in the cylindrical container and a carrying-out port for carrying out the same;

supply means for supplying a plurality of the cylindrical containers carried into said chamber through said carrying-in port;

first conveying means having a star wheel on which a plurality of support portions, each supporting said cylindrical container supplied by this supply means from its side surface, are provided on an outer periphery and a first rotating member for rotating this star wheel around its center axis and continuously conveying said cylindrical container;

a first electron beam accelerator for emitting an electron beam from the bottom surface portion side of said cylindrical container during conveyance by this first conveying means;

first reversing means for receiving said cylindrical container from said first conveying means and reversing its cylindrical shaft core by approximately 90 degrees;

second conveying means having a chucking member for receiving said cylindrical container from this first reversing means and supporting the cylindrical container from the bottom surface portion side by chucking, a third rotating member for rotating this chucking member together with said cylindrical container supported by the chucking member along the cylindrical shaft core of the cylindrical container, and a second transfer member for transferring said chucking member together with said cylindrical container supported by the chucking member in a direction intersecting the cylindrical shaft core of the cylindrical container and continuously conveying said cylindrical container;

a second electron beam accelerator for emitting the electron beam over the entire periphery from the side surface portion side of said cylindrical container during conveyance by this second conveying means;

a third electron beam accelerator for emitting the electron beam from the opening portion side to the inner surface portion of said cylindrical container during conveyance by said second conveying means;

second reversing means for receiving said cylindrical container from said second conveying means and reversing its cylindrical shaft core by approximately 90 degrees again; and carrying-out means for receiving said cylindrical container from this second reversing means and carrying out the cylindrical container to the outside of said chamber through said carrying-out port.

9. A continuous sterilization system comprising:

a chamber having a carrying-in port for carrying in the cylindrical container and a carrying-out port for carrying out the same;

supply means for supplying a plurality of the cylindrical containers carried into said chamber through said carrying-in port;

first reversing means for receiving said cylindrical container from said supply means and reversing its cylindrical shaft core by approximately 90 degrees;

second conveying means having a suction member for receiving said cylindrical container from this first reversing means and supporting the same from its bottom surface by vacuum-suctioning, a second rotating member for rotating this suction member together with said cylindrical container supported by the suction member along the cylindrical shaft core of the cylindrical container, and a first transfer member for transferring said suction member together with said cylindrical container supported by the suction member in a direction intersecting the cylindrical shaft core of the cylindrical container and continuously conveying said cylindrical container;

a second electron beam accelerator for emitting the electron beam over the entire periphery from the side surface portion side of said cylindrical container during conveyance by this second conveying means;

a third electron beam accelerator for emitting the electron beam from the opening portion side to the inner surface portion of said cylindrical container during conveyance by said second conveying means;

second reversing means for receiving said cylindrical container from said second conveying means and reversing its cylindrical shaft core by approximately 90 degrees again;

first conveying means having a star wheel on which a plurality of support portions, each receiving said cylindrical container from this second reversing means and supporting the cylindrical container from its side surface, are provided on an outer periphery and a first rotating member for rotating this star wheel around its center axis and continuously conveying said cylindrical container;

a first electron beam accelerator for emitting an electron beam from the bottom surface portion side of said cylindrical container during conveyance by this first conveying means; and carrying-out means for receiving said cylindrical container from said first conveying means and carrying out the cylindrical container to the outside of said chamber through said carrying-out port.

10. A continuous sterilization system comprising:
a chamber having a carrying-in port for carrying in the cylindrical container and a carrying-out port for carrying out the same;
supply means for supplying a plurality of the cylindrical containers carried into said chamber through said carrying-in port;
first reversing means for receiving said cylindrical container from said supply means and reversing its cylindrical shaft core by approximately 90 degrees;
second conveying means having a chucking member for receiving said cylindrical container from this first reversing means and supporting the cylindrical container from the bottom surface portion side by chucking, a third rotating member for rotating this chucking member together with said cylindrical container supported by the chucking member along the cylindrical shaft core of the cylindrical container, and a second transfer member for transferring said chucking member together with said cylindrical container supported by the chucking member in a direction intersecting the cylindrical shaft core of the cylindrical container and continuously conveying said cylindrical container;
a second electron beam accelerator for emitting the electron beam over the entire periphery from the side surface portion side of said cylindrical container during conveyance by this second conveying means;
a third electron beam accelerator for emitting the electron beam from the opening portion side to the inner surface portion of said cylindrical container during conveyance by said second conveying means;
second reversing means for receiving said cylindrical container from said second conveying means and reversing its cylindrical shaft core by approximately 90 degrees again;
first conveying means having a star wheel on which a plurality of support portions, each receiving said cylindrical container from this second reversing means and supporting the cylindrical container from its side surface, are provided on an outer periphery and a first rotating member for rotating this star wheel around its center axis and continuously conveying said cylindrical container;
a first electron beam accelerator for emitting an electron beam from the bottom surface portion side of said cylindrical container during conveyance by this first conveying means; and
carrying-out means for receiving said cylindrical container from said first conveying means and carrying out the cylindrical container to the outside of said chamber through said carrying-out port.

* * * * *